US006841386B2

(12) United States Patent
Kraus et al.

(10) Patent No.: US 6,841,386 B2
(45) Date of Patent: Jan. 11, 2005

(54) MODULATION OF PRIMARY STEM CELL DIFFERENTIATION USING AN INSULIN-LIKE GROWTH FACTOR BINDING PROTEIN

(75) Inventors: Morey Kraus, Jefferson, MA (US); Hongkui Deng, Framingham, MA (US); Liqin Liu, Framingham, MA (US)

(73) Assignee: Viacell, Inc., Worcester, MA (US)

(*) Notice: Subject to any disclaimer, the term of this patent is extended or adjusted under 35 U.S.C. 154(b) by 0 days.

(21) Appl. No.: 09/962,026

(22) Filed: Sep. 24, 2001

(65) Prior Publication Data

US 2002/0177227 A1 Nov. 28, 2002

Related U.S. Application Data

(60) Provisional application No. 60/282,973, filed on Apr. 10, 2001.

(51) Int. Cl.[7] ............................. C07K 14/00; C12N 5/00; C12N 5/02; C12N 5/06; C12N 5/08
(52) U.S. Cl. .............................. 435/375; 435/4; 435/325; 435/377; 530/350; 530/351; 530/399; 424/184.1; 514/3
(58) Field of Search ........................ 530/300, 350, 530/351, 399; 435/4, 7.1, 325, 375, 377; 424/185.1; 514/3

(56) References Cited

U.S. PATENT DOCUMENTS

| | | | |
|---|---|---|---|
| 5,212,074 A | 5/1993 | Kiefer et al. | 435/69.6 |
| 5,527,776 A | 6/1996 | Carlino et al. | 514/12 |
| 5,643,788 A | 7/1997 | Baserga et al. | 435/325 |
| 5,837,675 A | 11/1998 | Brox | 514/8 |
| 5,973,115 A | 10/1999 | Clemmons et al. | 530/350 |
| 6,017,885 A | 1/2000 | Bagi et al. | 514/12 |
| 6,121,416 A | 9/2000 | Clark et al. | 530/326 |
| 6,274,562 B1 * | 8/2001 | Baserga et al. | 514/44 |

FOREIGN PATENT DOCUMENTS

WO    WO 95/08567    3/1995

OTHER PUBLICATIONS

Arsenijevic et al. Insulin–like growth factor–I is a differentiation factor for postmitotic CNS stem cell–derived neuronal precursors: distinct actions from those of brain–derived neurotrophic factor. J Neurosci. 18(6):2118–2128, 1998.*
Baxter, RC. Insulin–like growth factor (IGF)–binding proteins: interactions with IGFs and intrinsic bioactivities. Am J Physiol Endocrinol Metab. 278(6):E967–976, 2000.*
Drago et al. Fibroblast growth factor–mediated proliferation of central nervous system precursors depends on endogenous production of insulin–like growth factor I. Proc Natl Acad Sci U S A. 88(6):2199–2203, 1991.*
Murphy, LJ. Insulin–like growth factor–binding proteins: functional diversity or redundancy? J Mol Endocrinol. 21(2):97–107, 1998.*

Pampusch et al. Effect of recombinant porcine IGF–binding protein–3 on proliferation of embryonic porcine myogenic cell cultures in the presence and absence of IGF–I. J Endocrinol. 176(2):227–235, 2003.*
Pell et al. Enhancement of insulin–like growth factor I activity by novel antisera: potential structure/function interactions. Endocrinology. 141(2):741–751, 2000.*
Spagnoli et al. Antiproliferative effects of insulin–like growth factor–binding protein–3 in mesenchymal chondrogenic cell line RCJ3.1C5.18. relationship to differentiation stage. J Biol Chem. 276(8):5533–5540, 2001.*
Grellier et al., "Characterization of Insulin–Like Growth Factor Binding Proteins (IGFBP) and Regulation of IGFBP–4 in Bone Marrow Stromal Cells," *British Journal of Haematology* 90:249–257 (1995).
Hansson et al., "Immunohistochemical Localization of Insulin–Like Growth Factor I in the Adult Rat," *Histochemistry* 89:403–410 (1988).
Hashimoto et al., "Binding Sites and Binding Properties of Binary and Ternary Complexes of Insulin–Like Growth Factor–II (IGF–II), IGF–Binding Protein–3, and Acid–Labile Subunit," *The Journal of Biological Chemistry* 272:27936–27942 (1997).
Hossner et al., "Insulin–Like Growth Factor (IGF)–I and –II and IGFPB Secretion by Ovine Satellite Cell Strains Grown Alone or in Coculture with 3T3–L1 Preadipocytes," *In Vitro Cell. Biol. Anim.* 33:791–795 (1997).
Huang, S. and L. Terstappen, "Formation of Haematopoietic Microenvironment and Haematopoietic Stem Cells from Single Human Bone Marrow Stem Cells," *Nature* 360:745–749 (1992).
Hughes et al., "The Insulin–Like Growth Factors (IGFs) in Follicular Fluid are Predominantly Bound in the Ternary Complex," *Journal of Endocrinology.* 155:R1–R4 (1997).
James et al., "Insulin–Like Growth Factor Binding Protein–5 Modulates Muscle Differentiation Through an Insulin–Like Growth Factor–Dependent Mechanism," *The Journal of Cell Biology* 133:683–693 (1996).
Kanatani et al., "Stimulatory Effect of Insulin–Like Growth Factor Binding Protein–5 on Mouse Osteoclast Formation and Osteoclastic Bone–Resorbing Activity," *Journal of Bone and Mineral Research* 15:902–910 (2000).
Lavranos et al., "Effects of Insulin–Like Growth Factors and Binding Protein 1 on Bovine Granulosa Cell Division in Anchorage–Independent Culture," *Journal of Reproduction and Fertility* 107:221–228 (1996).
Leal et al., "The Type V Transforming Growth Factor β Receptor is the Putative Insulin–Like Growth Factor–Binding Protein 3 Receptor," *The Journal of Biological Chemistry* 272:20572–20576 (1997).

(List continued on next page.)

*Primary Examiner*—Lorraine Spector
*Assistant Examiner*—Bridget E. Bunner
(74) *Attorney, Agent, or Firm*—Paul T. Clark; Clark & Elbing LLP

(57) ABSTRACT

The present invention features methods of modulating primary stem cell differentiation in culture by altering the endogenous activity of an insulin-like growth factor.

9 Claims, 13 Drawing Sheets

OTHER PUBLICATIONS

Li et al., "Regulation of Myeloid Growth and Differentiation by the Insulin–Like Growth Factor I Receptor," *Endocrinology* 138:362–368 (1997).

Long et al., "Involvement of Insulin–Like Growth Factor–1 and Its Binding Proteins in Proliferation and Differentiation of Murine Bone Marrow–Derived Macrophage Precursors," *Endocrine* 9:185–192 (1998).

Merchav et al., "Enhancement of Human Granulopoieses in Vitro by Biosynthetic Insulin–Like Growth Factor I/Somatomedin C and Human Growth Hormone," *J. Clin. Invest.* 81:791–797 (1988).

Merchav et al., "Enhancement of Erythropoiesis in Vitro by Human Growth Hormone is Mediated by Insulin–Like Growth Factor I," *British Journal of Haematology* 70:267–271 (1988).

Merchav et al., "Comparative Studies of the Erythroid–Potentiating Effects of Biosynthetic Human Insulin–Like Growth Factors–I and –II," *Journal of Clinical Endocrinology and Metabolism* 74:447–452 (1992).

Merchav et al., "In–Vitro Response of Erythroid Progenitors from Children with Thalassaemia Major to Human Growth Hormone and Insulin–Like Growth Factor I," *Clinical Endocrinology* 39:207–211 (1993).

Merchav et al., "Comparative Studies of the Granulopoietic Enhancing Effects of Biosynthetic Human Insulin–Like Growth Factors I and II," *Journal of Cellular Physiology* 157:178–183 (1993).

Merchav, S., "The Haematopoietic Effects of Growth Hormone and Insulin–Like Growth Factor–I," *Journal of Pediatric Endocrinology And Metabolism* 11:677–685 (1998).

Rajah et al., "Insulin–Like Growth Factor (IGF)–Binding Protein–3 Induces Apoptosis and Mediates the Effects of Transforming Growth Factor–$\beta1$ on Programmed Cell Death Through a p53– and IGF–Independent Mechanism," *The Journal of Biological Chemistry*. 272:12181–12188 (1997).

Stewart et al., "Overexpression of Insulin–Like Growth Factor–II induces Accelerated Myoblast Differentiation," *Journal of Cellular Physiology* 169:23–32 (1996).

Ueki et al., "Inactivation of the Acid Labile Subunit Gene in Mice Results in Mild Retardation of Postnatal Growth Despite Profound Disruptions in the Circulating Insulin–Like Growth Factor System," *Proc. Natl. Acad. Sci. USA* 97:6868–6873 (2000).

Zumkeller, W. and S. Burdach "The Insulin–Like Growth Factor System in Normal and Malignant Hematopoietic Cells," *Blood* 94:3653–3657 (1999).

Zumkeller, W., "The Role of Growth Hormone and Insulin–Like Growth Factors for Placental Growth and Development," *Placenta* 21:451–467 (2000).

Holman and Baxter, "Insulin–Like Growth Factor Binding Protein–3: Factors Affecting Binary and Ternary Complex Formation," *Growth Regulation* 6:42–47 (1996).

MacDonald et al., "Growth Inhibition and Differentiation of the Human Colon Carcinoma Cell Line, Caco–2, by Constitutive Expression of Insulin–like Growth Factor Binding Protein–3," *J. Gastroenterology and Hepatology* 14:72–78 (1999).

* cited by examiner

1 = 0.5 days
2 = 7 days
3 = 7.5 days
4 = 14 days
5 = 14.5 days

MODULATION OF PRIMARY STEM CELL DIFFERENTIATION USING AN INSULIN-LIKE GROWTH FACTOR BINDING PROTEIN

CROSS REFERENCE TO RELATED APPLICATIONS

This application claims benefit of U.S. provisional patent application Ser. No. 60/282,973, filed on Apr. 10, 2001.

BACKGROUND OF THE INVENTION

The art of ex vivo culture of hematopoietic stem cells and their progeny has advanced considerably in recent years. Notably, the identification of stage-specific antigens on the surfaces of cells and of a variety of extrinsically acting cytokine cocktails that drive expansion of cell numbers, as well as the development of biological assays to detect the potency of various end products (i.e., cell types) of expansion have provided the fundamental tools and knowledge to explore more refined methods for the controlled modulation of the proliferation and differentiation of cells in culture. While the present state of the art in hematopoietic cultures allows for the expansion of large numbers of cells, such cultures can lead to the exhaustion of the stem cell and progenitor cell pools.

SUMMARY OF THE INVENTION

The preset invention takes a step forward in the understanding of the mechanisms by which hematopoietic stem cells and hematopoietic progenitor cells self-renew or undergo differentiation. We have identified a group of polypeptides (factors) that affects the expansion and differentiation of hematopoietic stem cells and progenitor cells in culture. Such factors work in several different ways. In some circumstances, a factor acts as a positive regulator that drives proliferation of hematopoietic stem cells and progenitor cells without significantly promoting differentiation. This class of factor decouples proliferation from differentiation. Alternatively, the factor may act as a negative regulator of differentiation, inhibiting cells from differentiating. In another alternative, the factor may be an anti-differentiation factor that functions by working against another factor that is promoting cell differentiation.

Thus, we have discovered that an endogenous differentiation factor, insulin-like growth factor-1 (IGF-1), interacts with an exogenous anti-differentiation factor that is specific for IGF-1, called insulin-like growth factor binding protein (IGFBP) to affect expansion and differentiation of hematopoietic cells in culture. IGFBP is produced by human brain microvascular endothelial cells (HBVECs, also abbreviated as HMVECs and HMVEC-Bs), a supporting stromal cell population that enhances expansion of hematopoietic stem cells and stem cell precursors in vitro (FIG. 12). We believe that another human protein, insulin-like growth factor-2 (IGF-2), interacts with IGFBP in a manner similar to IGF-1. For purposes of the preset invention, IGF-1, IGF-2, and analogs and fragments of these polypeptides that similarly interact with IGFBP are referred to as IGFs.

IGF-1 and -2, and IGFBP-1 to -6 are involved in the regulation of cellular proliferation and differentiation of many cell types. For example, IGFs have been shown to stimulate cell proliferation and differentiation in cultured neural stem cells, osteoprogenitors, adipocyte progenitors, myoblasts, and macrophage precursors. The actions of IGFs are determined by the availability of free IGFs to interact with the IGF receptors (IGF-I-R and IGF-II-R). IGFBPs comprise a family of proteins that bind IGFs with high affinity and specificity, and thereby regulate IGF-dependent actions.

By modulating the activity of IGF, it is possible to control the differentiation of hematopoietic stem cells and hematopoietic progenitor cells. The controlled modulation of proliferation and differentiation in the ex vivo culture of hematopoietic stem cells and their progeny are useful for cellular therapeutics for conditions and diseases including, but not limited to cancer, inborn genetic disorders, organ transplantation tolerance, immune enhancement, and tissue restoration.

Accordingly, in a first aspect, the invention features a method of modulating differentiation of a cultured primary stem cell, involving altering the endogenous activity of an insulin-like growth factor in the cell.

In a second aspect, the invention features a method of modulating differentiation of a cultured hematopoietic progenitor cell, involving altering the endogenous activity of an insulin-like growth factor in the cell.

In one embodiment of the above aspects of the invention, the alteration further involves the use of an insulin-like growth factor binding protein or acid-labile subunit. In another embodiment, the insulin-like growth factor is insulin-like growth factor-1 or insulin-like growth factor-2, and the insulin-like growth factor binding protein is any of insulin-like growth factor binding protein-1, insulin-like growth factor binding protein-2, insulin-like growth factor binding protein-3, insulin-like growth factor binding protein-4, insulin-like growth factor binding protein-5, or insulin-like growth factor binding protein-6.

In other desirable embodiments of the above aspects of the invention, the modulation of differentiation of a cultured hematopoietic cell involves stimulating the differentiation of the cultured primary stem cell or hematopoietic progenitor cell, or it involves inhibiting the differentiation of the cultured primary stem cell or hematopoietic progenitor cell.

In a third aspect, the invention features a method of inhibiting differentiation of a cultured primary stem cell, involving the step of contacting the cell with an insulin-like growth factor binding protein.

In a fourth aspect, the invention features a method of inhibiting differentiation of a cultured hematopoietic progenitor cell, involving the step of contacting the cell with an insulin-like growth factor binding protein.

In one embodiment of the third or fourth aspect of the invention, the insulin-like growth factor binding protein is insulin-like growth factor binding protein-3.

In a fifth aspect, the invention features a method of inhibiting net differentiation of primary stem cells in culture, involving reducing the number of insulin-like growth factor-1-producing cells in the culture by reducing the endogenous activity of an insulin-like growth factor, by selectively reducing cells that produce an insulin-like growth factor from the culture. This reduction is achieved, for example, by removing or killing the cells that produce an insulin-like growth factor.

In a sixth aspect, the invention features a method of inhibiting net differentiation of hematopoietic progenitor cells in culture, involving reducing the number of insulin-like growth factor-1-producing cells in the culture by reducing the endogenous activity of an insulin-like growth factor, by selectively reducing cells that produce an insulin-like growth factor from the culture. This reduction is achieved, for example, by removing or killing the cells that produce an insulin-like growth factor.

In a seventh aspect, the invention features a method of modulating differentiation of primary stem cells in culture, involving altering the endogenous activity of an insulin-like growth factor, by introducing an antisense nucleic acid molecule that decreases the production of insulin-like growth factor in the culture.

In an eighth aspect, the invention features a method of modulating differentiation of hematopoietic progenitor cells in culture, involving altering the endogenous activity of an insulin-like growth factor, by introducing an antisense nucleic acid molecule that decreases the production of insulin-like growth factor in the culture.

In one embodiment of the seventh or eighth aspects of the invention, the antisense nucleic acid molecule is a molecule that binds to a nucleic acid encoding insulin-like growth factor-1, insulin-like growth factor-2, or the insulin-like growth factor-1 receptor. In another aspect, the antisense nucleic acid molecule is a molecule that binds to a nucleic acid encoding an insulin-like growth factor binding protein, for example, any of insulin-like growth factor binding proteins-1 through -6. The activity of an insulin-like growth factor may be modulated, for example, by altering the level of expression of the molecule against which an antisense nucleic acid is designed.

In a ninth aspect, the invention features a method of modulating differentiation of primary stem cells in culture, involving altering the level of an insulin-like growth factor in combination with an insulin-like growth factor binding protein.

In a tenth aspect, the invention features a method of modulating differentiation of hematopoietic progenitor cells in culture, involving altering the level of an insulin-like growth factor in combination with an insulin-like growth factor binding protein.

In an eleventh aspect, the invention features a method of modulating differentiation of cultured hematopoietic stem cells by altering the endogenous activity of an insulin-like growth factor by treating the cultured cell with insulin-like growth factor binding protein-3.

In a twelfth aspect, the invention features a method of modulating differentiation of cultured primary stem cells by altering the endogenous activity of an insulin-like growth factor by treating the cultured cell with insulin-like growth factor binding protein-3.

In a thirteenth aspect, the invention features a method of modulating differentiation of cultured hematopoietic progenitor cells by altering the endogenous activity of an insulin-like growth factor by treating the cultured cell with insulin-like growth factor binding protein-3.

In an fourteenth aspect, the invention features a method of modulating differentiation of primary stem cells in culture, involving altering the endogenous activity of an insulin-like growth factor binding protein, by introducing an antisense nucleic acid molecule that decreases the production of insulin-like growth factor binding protein in the culture.

In an embodiment of the fourteenth aspect, the method further features treatment with transforming growth factor-β (TGF-β).

In another embodiment of the fourteenth aspect, the primary stem cell is a hematopoietic stem cell.

In an fifteenth aspect, the invention features a method of modulating differentiation of hematopoietic progenitor cells in culture, involving altering the endogenous activity of an insulin-like growth factor binding protein, by introducing an antisense nucleic acid molecule that decreases the production of insulin-like growth factor binding protein in the culture.

In an embodiment of the fifteenth aspect, the method further features treatment with TGF-β.

In one embodiment of the fourteenth or fifteenth aspects of the invention, the antisense nucleic acid molecule is a molecule that binds to a nucleic acid encoding insulin-like growth factor binding protein-3. The activity of an insulin-like growth factor binding protein may be modulated, for example, by altering the level of expression of the molecule against which an antisense nucleic acid is designed.

In a sixteenth aspect, the invention features a method of modulating differentiation of primary stem cells in culture, involving altering the endogenous activity of an insulin-like growth factor binding protein, by introducing an antisense nucleic acid molecule that decreases the production of insulin-like growth factor binding protein in the culture in combination with TGF-β.

In a seventeenth aspect, the invention features a method of modulating differentiation of hematopoietic progenitor cells in culture, involving altering the endogenous activity of an insulin-like growth factor binding protein, by introducing an antisense nucleic acid molecule that decreases the production of insulin-like growth factor binding protein in the culture in combination with TGF-β.

In one embodiment of the sixteenth and seventeenth aspects of the invention, the antisense nucleic acid molecule is a molecule that binds to a nucleic acid encoding insulin-like growth factor binding protein-3. The activity of an insulin-like growth factor binding protein may be modulated, for example, by altering the level of expression of the molecule against which an antisense nucleic acid is designed.

An eighteenth aspect of the invention features a method for in vivo expansion of hematopoietic progenitor cells in a subject by modulating the differentiation of the hematopoietic stem cells. Modulation of the hematopoietic progenitor cells occurs by altering the endogenous activity of an insulin-like growth factor binding protein by administering an antisense nucleic acid molecule that decreases the production of insulin-like growth factor binding protein in a subject.

A nineteenth aspect of the invention features a method for in vivo expansion of primary stem cells in a subject by modulating the differentiation of the hematopoietic stem cells. Modulation of the primary stem cells occurs by altering the endogenous activity of an insulin-like growth factor binding protein by administering an antisense nucleic acid molecule that decreases the production of insulin-like growth factor binding protein in a subject.

In an embodiment of the eighteenth and nineteenth aspects of the invention, TGF-β is also administered to the subject.

A twentieth aspect of the invention features a method for ex vivo expansion of hematopoietic stem cells and administration of the hematopoietic stem cells to a subject. This aspect of the invention is performed by first isolating a population containing hematopoietic stem cells from the subject. Next, the differentiation and expansion of the cells is modulated by altering the endogenous activity of an insulin-like growth factor binding protein by introducing an antisense nucleic acid molecule that decreases the production of insulin-like growth factor binding protein into the culture. Finally, the modulated hematopoietic stem cells are administered to the subject. Descriptive methods for ex vivo expansion of hematopoietic stem cells can be found in U.S. Pat. Nos. 5,674,750 and 5,925,567, which are herein incorporated by reference.

In an embodiment of the twentieth aspect, the treatment occurs in combination with TGF-β.

In an embodiment of the nineteenth and twentieth aspects, the antisense nucleic acid molecule is a molecule that binds to a nucleic acid encoding insulin-like growth factor binding protein-3. The activity of an insulin-like growth factor binding protein may be modulated, for example, by altering the level of expression of the molecule against which an antisense nucleic acid is designed. In a further embodiment of the nineteenth and twentieth aspects, the subject is a mammal. In yet a further embodiment, the mammal is a human. In another embodiment of the nineteenth and twentieth aspects, the in vivo expansion of hematopoietic stem cells is used to restore or supplement an immune system or blood forming system that has been compromised by, e.g., irradiation therapy or chemotherapy.

In any of the above methods of the invention, the cultured primary stem cell or hematopoietic progenitor cell is mammalian, for example, human. In another desired embodiment of any of the first, third, fifth, seventh, or ninth aspects of the invention, the cultured primary cell is a hematopoietic stem cell.

By "endogenous activity of an insulin-like growth factor" is meant any biological activity of an insulin-like growth factor. Such biological activities include, but are not limited to, regulation of cell proliferation and differentiation.

By a "primary stem cell" is meant a cell capable of self-renewal and proliferation while maintaining its ability to differentiate into more than one type of cell. Examples of primary include, but are not limited to hematopoietic stem cells.

By a "hematopoietic stem cell" is meant a cell capable of self-renewal and proliferation while maintaining its ability to differentiate into specialized hematopoietic cells. Hematopoietic stem cells serve as a continuous source of new cells for the blood and immune system, and can be identified as a subset of those cells having a CD45$^+$, CD34$^{+/-}$, CD38$^-$ phenotype.

By a "hematopoietic progenitor cell" is meant a cell capable of differentiation into specialized hematopoietic cells that serve as a continuous source of new cells for the blood and immune system. Hematopoietic progenitor cells can be identified as those cells having a CD45$^+$, CD34$^+$ phenotype.

By "lin$^-$" is meant a cell that does not express any of the following markers: CD2, CD3, CD14, CD16, CD19, CD56, CD66B, and GlyA.

By a "compound," "test compound," or "candidate compound" is meant a chemical molecule, be it naturally-occurring or artificially-derived, and includes, for example, peptides, proteins, synthetic organic molecules, naturally-occurring organic molecules, nucleic acid molecules, anti-sense nucleic acid molecules, and components thereof.

By "transformation," "transfection," or "transduction" is meant any method for introducing foreign molecules into a cell, e.g., a bacterial, yeast, fungal, algal, plant, insect, or animal cell. Lipofection, DEAE-dextran-mediated transfection, microinjection, protoplast fusion, calcium phosphate precipitation, retroviral delivery, electroporation, and biolistic transformation are just a few of the methods known to those skilled in the art which may be used. In addition, a foreign molecule can be introduced into a cell using a cell penetrating peptide, for example, as described by Fawell et al. (Proc. Natl. Acad. Sci. U.S.A. 91:664–668, 1994) and Lindgren et al. (TIPS 21:99–103, 2000).

By "transformed cell," "transfected cell," or "transduced cell," is meant a cell (or a descendent of a cell) into which a nucleic acid has been introduced, by means of recombinant nucleic acid techniques.

By "promoter" is meant a minimal sequence sufficient to direct transcription. Also included in the invention are those promoter elements that are sufficient to render promoter-dependent gene expression controllable for cell type-specificity or tissue-specificity, or that are inducible by external signals or agents; such elements may be located in the 5' or 3' regions of the native gene.

By "operably linked" is meant that a gene and one or more regulatory sequences are connected in such a way as to permit gene expression when the appropriate molecules (e.g., transcriptional activator proteins) are bound to the regulatory sequences.

As used herein, by "modulating" is meant either increasing or decreasing the number of cells that differentiate in a given proliferating cell population. The cell population may be a primary stem cell, for example a hematopoietic cell population that is capable of undergoing differentiation or self-renewal. It will be appreciated that the degree of the modulation of differentiation provided by a differentiation-modulating compound in a given assay will vary, but that one skilled in the art can determine the statistically significant change in the level of differentiation that identifies a compound that increases or decreases differentiation of a cultured primary stem cell, for example, a hematopoietic stem cell, or a hematopoietic progenitor cell population. Desirably, differentiation is decreased by at least 20%, more desirably, by at least, 40%, 50%, or 75%, and, most desirably, by at least 90%, relative to a control sample that was not administered the differentiation-modulating test compound. Also as used herein, desirably, differentiation is increased by at least 1.5-fold to 2-fold, more desirably, by at least 3-fold, and most desirably, by at least 5-fold, relative to a control sample that was not administered the differentiation-modulating test compound.

By "antisense," as used herein in reference to nucleic acids, is meant a nucleic acid molecule, regardless of length, that is complementary to the coding strand or mRNA of a target gene, for example, a gene that modulates differentiation. The antisense nucleic acid is capable of modulating differentiation when present in a cell, for example, a primary stem cell, such as a hematopoietic stem cell, or a hematopoietic progenitor cell that is otherwise capable of producing the differentiation factor. Such modulation decreases the concentration of solubilized differentiation factor that would otherwise affect neighboring cells. An antisense nucleic acid molecule may decrease the activity of a polypeptide encoded by the target gene. Desirably the decrease is at least 10%, relative to a control, more desirably at least 25%, 50%, or 75%, and most desirably at least 90% or 99% or more. An antisense nucleic acid molecule may comprise from about 8 to 30 nucleotides. An antisense nucleic acid may also contain at least 40, 60, 85, 120, or more consecutive nucleotides that are complementary to a target mRNA or DNA, and may be as long as the full-length target gene or mRNA. The antisense nucleic acid may contain a modified backbone, for example, phosphorothioate, phosphorodithioate, or other modified backbones known in the art, or may contain non-natural internucleoside linkages.

As used herein, by "analog" is meant a polypeptide that functions in a manner similar to a desired or selected polypeptide. Analogs can differ from the naturally occurring polypeptide, for example, an IGFBP or an acid-labile subunit, by amino acid sequence differences, by post-translational modifications, or by both. Analogs of the invention will generally exhibit at least 85%, 90%, 95%, or even 99% identity with all or part of the naturally-occurring selected polypeptide sequence. The length of sequence comparison is at least 5, 15, 25, or 50 amino acid residues, or the full length of the polypeptide sequence. Modifications include in vivo and in vitro chemical derivatization of polypeptides, e.g., acetylation, carboxylation, phosphorylation, pegylation, or glycosylation; such modifications may occur during polypeptide synthesis or processing or following treatment with isolated modifying enzymes.

Analogs can also differ from the naturally occurring IGFBP or acid-labile subunit polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., *Current Protocols in Molecular Biology*, John Wiley & Sons, New York, N.Y., 1998). Also included are cyclized peptides, molecules, and analogs that contain residues other than L-amino acids, e.g., D-amino acids or non-naturally occurring or synthetic amino acids, e.g., β or γ amino acids.

By a "substantially pure polypeptide" is meant a polypeptide (or a fragment thereof) that has been separated from the components that naturally accompany it. Typically, the polypeptide is substantially pure when it is at least 60%, by weight, free from the proteins and naturally-occurring organic molecules with which it is naturally associated. Desirably, the polypeptide is an IGFBP or an acid-labile subunit polypeptide that is at least 75%, 90%, or 99%, by weight, pure. A substantially pure IGFBP or an acid-labile subunit polypeptide may be obtained, for example, by extraction from a natural source (e.g., a primary stem cell, a hematopoietic cell or a stromal cell), by expression of a recombinant nucleic acid encoding the desired polypeptide, or by chemically synthesizing the polypeptide. Purity can be measured by any appropriate method, e.g., by column chromatography, polyacrylamide gel electrophoresis, or HPLC analysis.

A protein is substantially free of naturally associated components when it is separated from those contaminants that accompany it in its natural state. Thus, a protein that is chemically synthesized or produced in a cellular system different from the cell from which it naturally originates will be substantially free from its naturally associated components. Accordingly, substantially pure polypeptides not only include those derived from eukaryotic organisms but also those synthesized in *E. coli* or other prokaryotes.

By "specifically binds" is meant an antibody that recognizes and binds exclusively a target polypeptide, for example, an IGF, an IGFBP, or an acid-labile subunit polypeptide, but that does not substantially recognize and bind other molecules (e.g., other polypeptides) in a sample, e.g., a biological sample, that naturally includes that protein. As used herein, an antibody to IGF does not bind IGFBP or acid-labile subunit; an antibody that binds IGFBP does not bind IGF or acid-labile subunit; and an antibody that binds acid-labile subunit does not bind IGF or IGFBP.

DETAILED DESCRIPTION

Support for the theory that there are factors that regulate hematopoietic stem cell and progenitor cell differentiation comes from co-culturing such cells with different stromal cell types or different stromal elements. For example, human brain microvascular endothelial cells (HBVECs) appear to support rapid expansion of progenitor cells, but over time these cells are not able to maintain the expansion of the progenitor cells.

Another path of evidence that suggests that there is a way to increase the hematopoietic stem cell/progenitor cell pool is from in vivo experiments. Some mouse strains have a higher stem cell content than other mouse strains. There has been significant interest in determining if the mice with the higher stem cell counts possess a factor in their stroma or a factor that is produced systemically or in a local microenvironment that allows increased stem cell content to occur.

We have developed a system to identify positive, negative, and anti-differentiation factors that can regulate differentiation of primary stem cells, for example, hematopoietic stem cells, as well as hematopoietic progenitor cells. This system, described in detail below, involves a forward genetic strategy of functional expression cloning, and uses a seed population or a co-culture population of HBVECs in combination with $CD34^+CD38^-$ cells (for example, human umbilical cord cells or bone marrow cells). The results of this screen have led to the identification of various methods that can be used to modulate differentiation of primary stem cells, such as hematopoietic stem cells, and hematopoietic progenitor cells.

One such method involves the use of antisense nucleic acid molecules that bind to a nucleic acid molecule encoding insulin-like growth factor binding protein-3 (IGFBP-3). In some instances, antisense nucleic acid molecules that bind to IGFBP-3 can be used alone, or in combination with factors that stimulate the expansion of desired cell types. Insulin-like growth factor-1 is an endogenous differentiation factor that interacts with IGFBP-3, which is an anti-differentiation factor. This interaction, in addition to preventing differentiation, promotes expansion of hematopoietic cells in culture, specifically $CD34^+CD38^-$ cells.

Figure 11:
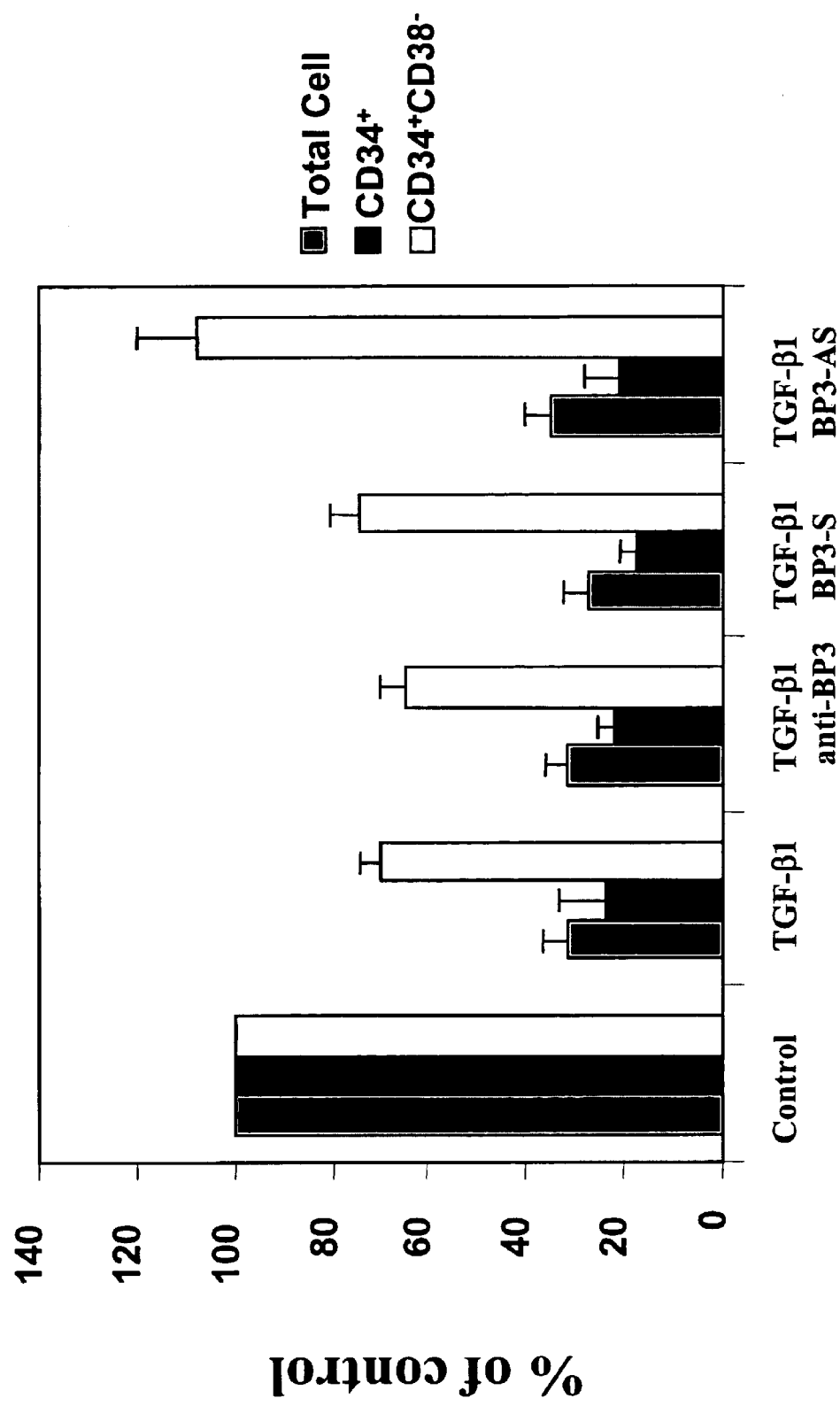
FIG. 11 is a graph of the effect on purified cord blood $CD34^+CD38^-Lin^-$ cells of exogenously added TGF-β1 alone, or in combination with either an IGFBP3 neutralizing antibody, or sense or antisense IGFBP3 oligomers. $CD34^+CD38^-Lin^-$ cells were cultured in IMDM plus 10% FBS medium containing 100 ng/ml of hematopoietic cytokines (SCF, Flt-3L, TPO) in the absence or presence of TGF-β1 at 5 ng/ml alone, or combined with IGFBP3 neutralizing antibody, or 20 μg/ml of IGFBP3 sense or antisense oligomers. Six-days later, the cultured cells were harvested and FACS analysis were performed to evaluate total cell numbers, $CD34^+$ and $CD34^+CD38^-$ populations.
Figure 12:
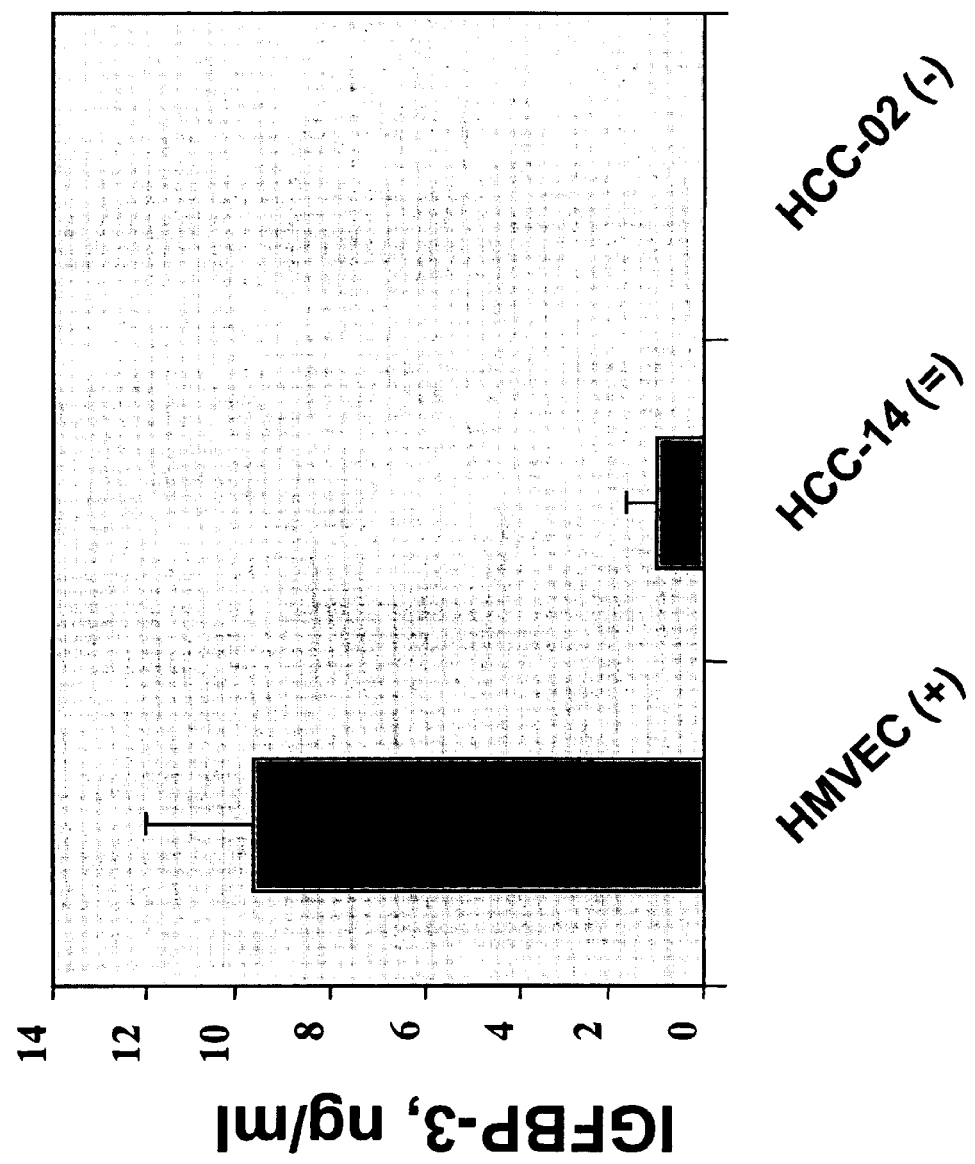
FIG. 12 is a graph demonstrating that IGFBP-3 is differentially secreted by the HBVECs.

Antisense IGFBP-3 can be used in conjunction with TGF-β, which acts to reduce the proliferation of the total cell population in culture, while allowing proliferation and expansion of hematopoietic cells in culture (FIG. 11). The use of TGF-β for this purpose, at least at some phase of the cell culture process, can be advantageous because the decrease in the total cell population has the effect of decreasing the amount of cell-derived inhibiting factors that can inhibit the growth of the target cell population. The presence of TGF-β, then, can be used to preferentially promote the expansion of $CD34^+CD38^-$ hematopoietic cells. The ability to preferentially expand specific populations of hematopoietic cells provides a powerful therapeutic advantage, especially in the treatment and prevention of diseases, to restore or supplement an immune system and/or blood forming system compromised by, e.g., radiation or chemotherapy, and as a valuable tool in the design, development, and testing of diagnostic and therapeutic agents used in the treatment of immune system and/or blood forming disorders.

The present invention is illustrated by the following examples, which are in no way intended to be limiting of the invention.

EXAMPLES

Example 1

Elutriation of HBVECs and Extinction Assay for the Identification of Factors that Modulate Hematopoietic Cell Differentiation As noted above, HBVECs are cells that modulate hematopoietic cell differentiation. To identify specific differentiation-modulatory factors produced by HBVECs (Clonetics Corp., Walkersville, Md.), these cells were elutriated into fourteen different fractions, named fractions HCC-01 to HCC-14. The different HBVEC elutriated fractions were then subjected to an extinction assay in order to determine the effect of each cell fraction on the extinction of a population of $CD34^+CD38^-$ cells combined with the fraction, and also to discriminate between elutriated HBVEC fractions with more or less positive, neutral, or negative activity. This assay was carried out as follows. Each of the fourteen different elutriated fractions was expanded into clonal pools that were later plated into tissue culture dishes. $CD34^{+/-}$, $CD38^-$, $lin^-$ cells (human umbilical cord blood cells) were placed on top of the elutriated cell fractions. The cells were then cultured in media containing the differentiation factors IL-3 and GM-CSF, and differentiation serum (fetal bovine serum; HyClone Laboratories, Inc., Logan, Utah).

The different elutriated HBVEC fractions then analyzed over time to determine which fractions supported a reduced rate of differentiation of $CD34^+CD38^-$ cells under the above-described extreme differentiation regimens. A negative elutriated HBVEC fraction, when used together with the other differentiation factors and differentiation serum, resulted in the rapid extinction of the $CD34^+CD38^-$ cell population, relative to the total cell population, as assayed by flow cytometry. A positive elutriated HBVEC fraction, when used together with the other differentiation factors and differentiation serum, maintained or increased the $CD34^+CD38^-$ cell population, relative to the total cell population.

Figure 1:
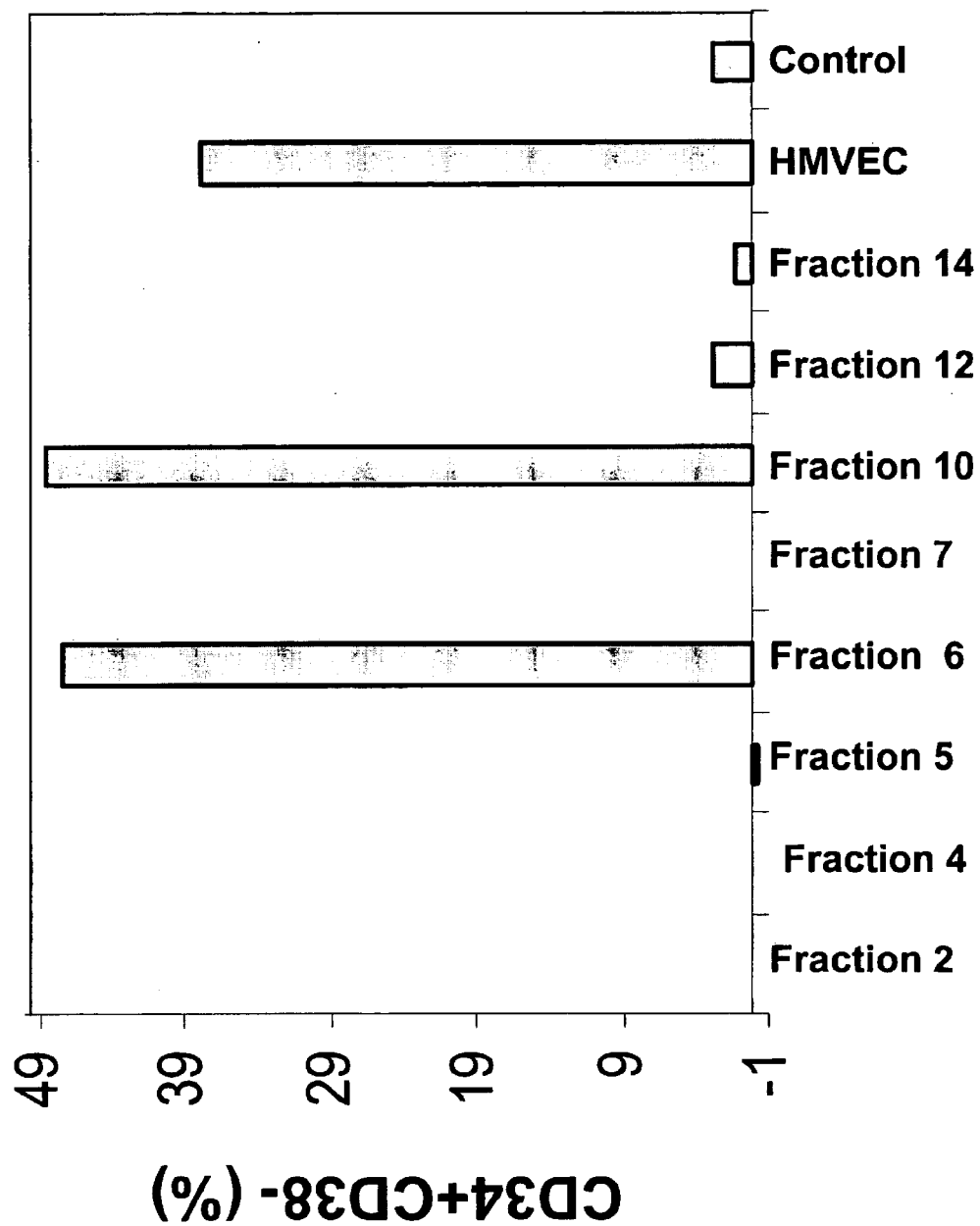
FIG. 1 is a graph of the percent of $CD34^+CD38^-$ cells present in the total population of cells after four days of co-culture with different elutriated fractions of HBVECs. "HMVEC" is HBVECs used as a positive control, and "control" is a suspension culture of only $CD34^{+/-}CD38^-lin^-$ cells, used as an additional control.

The extinction assay identified ten HBVEC elutriated fractions (HCC-01, HCC-02, HCC-03, HCC-04, HCC-05, HCC-07, HCC-08, HCC-09, HCC-11, and HCC-13) that had a significant negative effect on culture of the $CD34^+CD38^-$ cells, resulting in the rapid extinction of those cells. Two fractions, HCC-12 and HCC-14 (shown as fractions 12 and 14, respectively, in FIG. 1) were of neutral nature, in that there was a slow extinction of the $CD34^+CD38^-$ cells, but the extinction was not as fast as the extinction displayed by the negative fractions. In addition, fractions HCC-06 and HCC-10 (shown as fractions 6 and 10, respectively, in FIG. 1) decreased the rate of differentiation of $CD34^+CD38^-$ cells. Therefore, elutriated fractions HCC-06 and HCC-10 were considered to be positive fractions. These results are summarized in FIG. 1, where elutriated fractions (HCC-06 and HCC-10) are shown to decrease the differentiation of $CD34^+CD38^-$ cells as well or better than the positive control HMVECs (also known as HBVECs), which were known to decrease the differentiation of $CD34^+CD38^-$ cell populations. An additional control used in this study was $CD34^{+/-}CD38^-Lin^-$ cells alone in a suspension culture. At the end of the assay, these cells were slowly depleted of $CD34^+CD38^-$ cells. Fractions 12 and 14 (HCC-12 and HCC-14, respectively) resulted in a slower extinction rate of $CD34^+$ $CD38^-$ cells, similar to that of the control culture, and were therefore considered to be neutral fractions.

Figure 2:
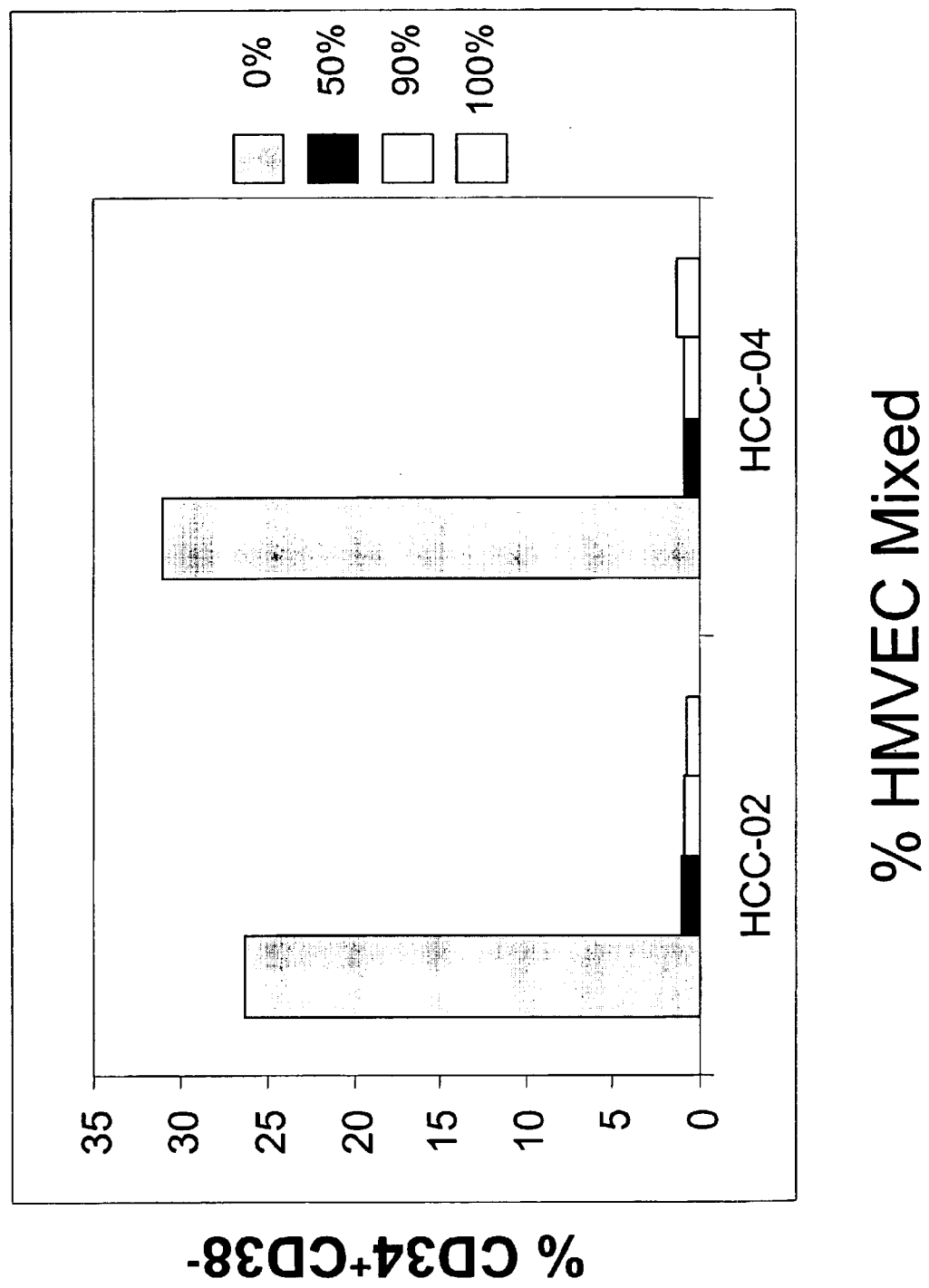
FIG. 2 is a graph of the percent of $CD34^+CD38^-$ cells present in the total population of cells after four days of co-culture with various percentages of the elutriated fractions HCC-02 or HCC-04.

The ability of the negative elutriated fractions to negatively regulate expansion of $CD34^+CD38^-$ cells was further examined by mixing HBVECs that increase the population of $CD34^+CD38^-$ cells with the elutriated fractions HCC-02 and HCC-04 such that the final population of mixed cells contained 0% (positive control), 50%, 90%, or 100% of either HCC-02 or HCC-04 cell fractions. $CD34^{+/-}CD38^-$ $Lin^-$ cells were then added to the cultures, and the cultures were monitored for the presence of $CD34^+CD38^-$ cells after 4 days of culture (FIG. 2). The presence of any amount of elutriated cell fraction HCC-02 or HCC-04 antagonized the effect of the HBVECs, and resulted in the extinction of $CD34^+CD38^-$ cells. These results demonstrate that the negative fractions rapidly decrease the ability of $CD34^+CD38^-$ cells to be maintained or increased relative to the total culture population.

Figure 3:
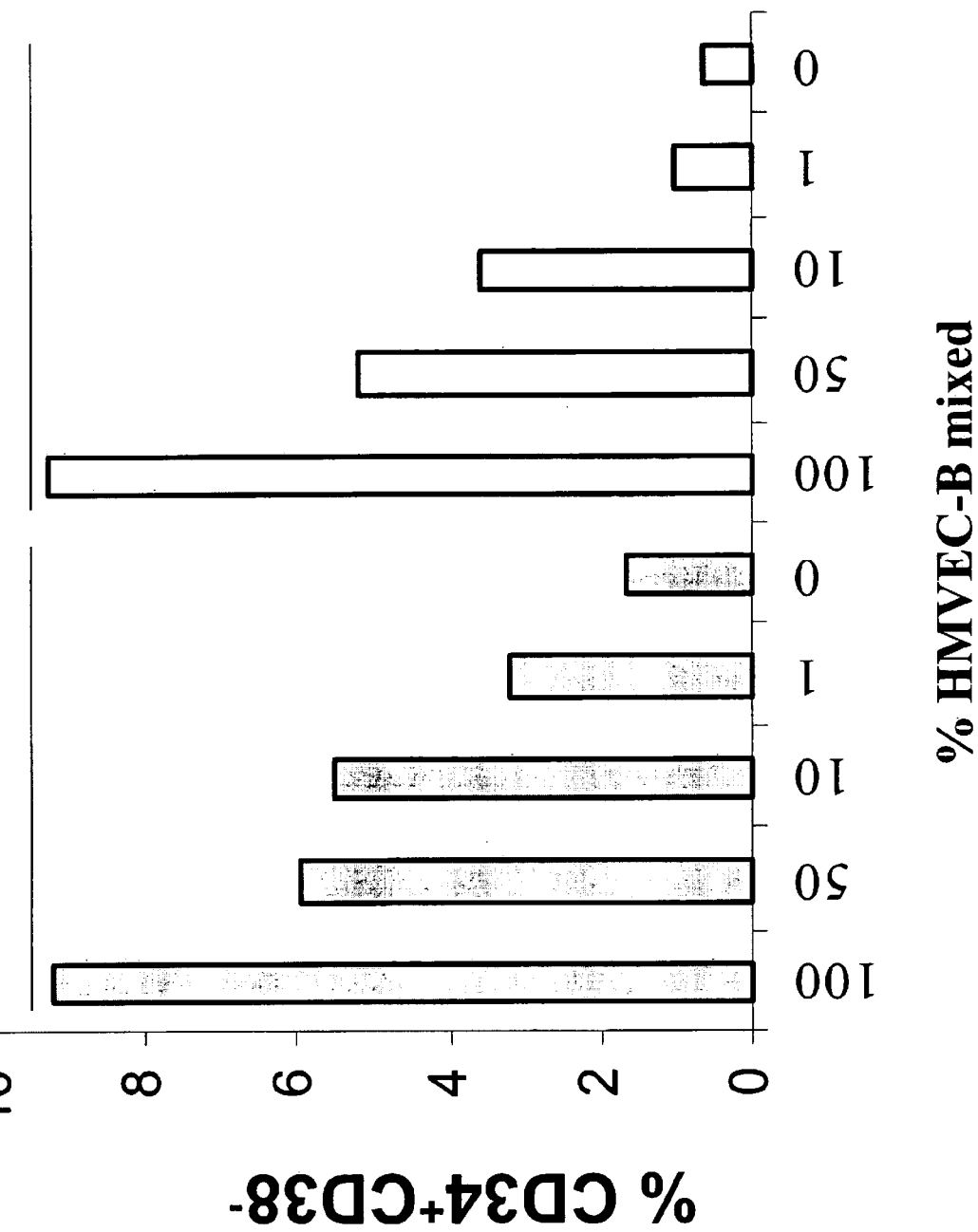
FIG. 3 is a graph of the percent of $CD34^+CD38^-$ cells present in the total population of cells after four days of co-culture with various percentages of the elutriated fractions HCC-12 or HCC-14.

The above-described cell mixing assay was also performed using neutral elutriated HCC-12 and HCC-14 cell fractions (FIG. 3). HBVECs were mixed with HCC-12 or HCC-14 cell fractions such that the mixture contained 100% (positive control), 50%, 10%, 1%, or 0% HBVECs. $CD34^{+/-}$ $CD38^-Lin^-$ cells were then added to the cultures, and the cultures were monitored over 7 days for the presence of $CD34^+CD38^-$ cells by flow cytometry, as a percentage of the total cell population. The mixture containing 50% HBVECs affected the population of $CD34^+CD38^-$ cells by diluting the effect of the HBVECs in a concentration-dependent manner. The population of HBVECs in the mixed population could be decreased to as little as 1% of the total population of cells, and a small effect on the population of $CD34^+CD38^-$ cells was still seen. The results of this assay confirm that elutriated HCC-12 and HCC-14 cell fractions behave similar to suspension cultures of $CD34^{+/-}CD38^-Lin^-$ cells that do not contain any HBVECs. As these neutral cells do not possess factors that modulate hematopoietic cell differentiation, they can be used for functional screening of factors that modulate expansion or differentiation of hematopoietic stem cells or progenitor cells, while representing a similar genetic background to the control HBVECs, as described below.

Example 2

Optimization of the Extinction Assay

Figure 4:
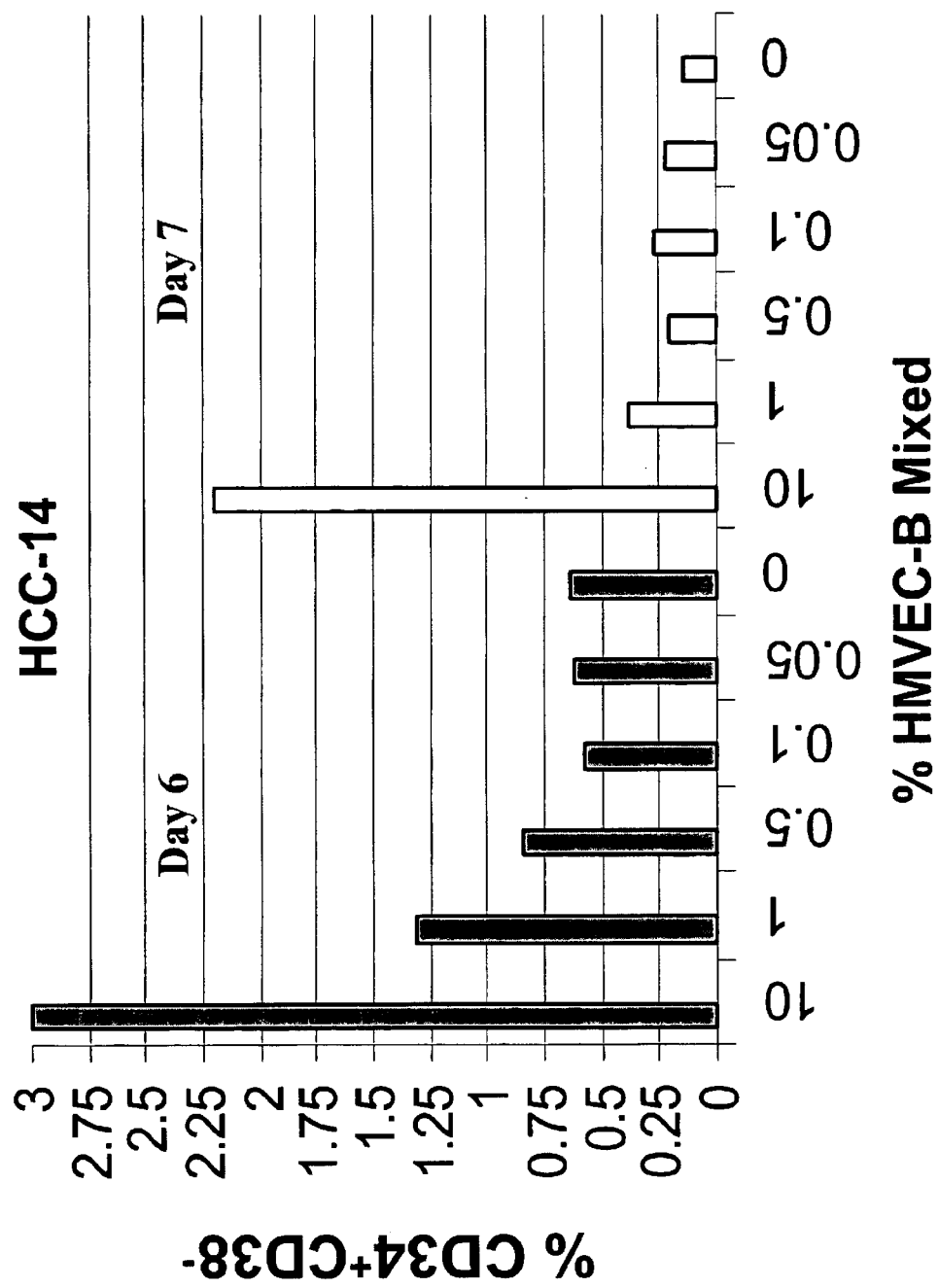
FIG. 4 is a graph of the percent of $CD34^+CD38^-$ cells present in the total population of cells after 6 or 7 days of co-culture with various percentages of elutriated HBVECs (HCC-14 fraction).

Conditions for optimizing the detection of expanded or maintained populations of $CD34^+CD38^-$ cells were also determined. HBVECs were mixed with elutriated cell fraction HCC-14 such that the mixture contained 10%, 1%, 0.5%, 0.1%, 0.05% or 0% HBVECs. $CD34^{+/-}CD38^-Lin^-$ cells were added to the cultures, and the presence of $CD34^+$ $CD38^-$ cells was assessed each day by flow cytometry, as a percentage of the total cell population. The results of this assay revealed that day 6 was optimal for detecting differences in $CD34^+CD38^-$ cells present in samples with between 1% and 10%, 0.5% and 1%, and 0.1% or less mixing with HBVECs (FIG. 4). These results also demonstrate that a 1% positive response (1% presence of $CD34^+$ $CD38^-$ cells) could be detected using the mixing experiment. Accordingly, a functional genomics approach that could measure such a level of $CD34^+CD38^-$ cells could be constructed.

To further develop the assay conditions for identifying factors that modulate differentiation, the differentiation effect of sera in the extinction assay was examined. For the purpose of this assay, the cells of this system require sera. Without sera, cells become $CD38^-$ in a conversion fashion; this CD marker display is not based on differentiation or the production of cells, but rather, the cells simply do not express the CD38 marker. Therefore, it was important in this study to use sera in the screening assays.

Figure 5:
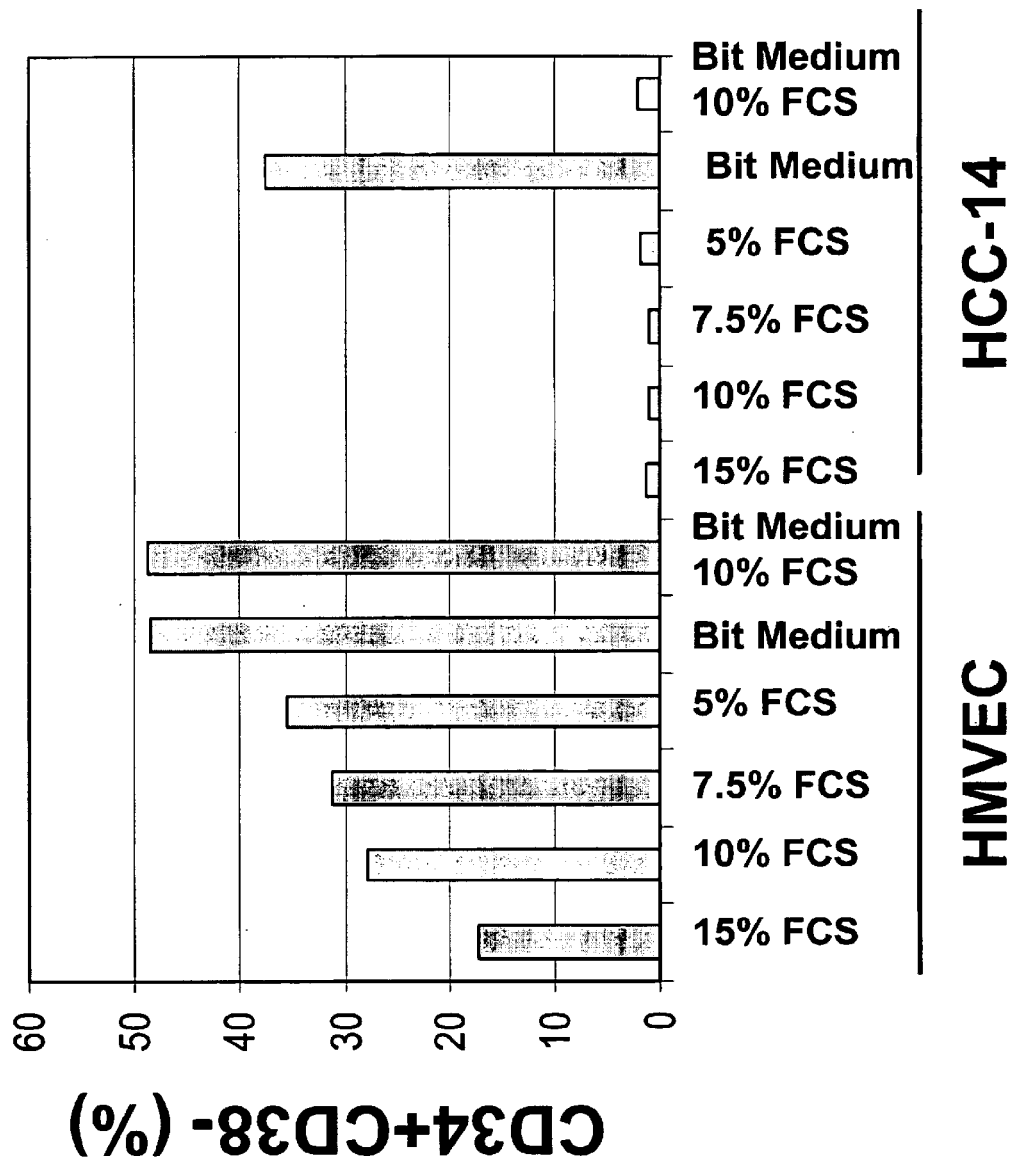
FIG. 5 is a graph of the effect of fetal calf serum (FCS) on the percent of $CD34^+CD38^-$ cells present in the total population of cells after 5 days of co-culture with human microvascular endothelial cells or the elutriated HCC-14 fraction.

The effect of sera (fetal calf serum; FCS) on the number of $CD34^+CD38^-$ cells was examined using the positive HBVECs and the neutral cells of elutriated fraction HCC-14 (FIG. 5). In the HBVEC system, as increased amounts of sera were used in the extinction assay (ranging from 5% to 15% FCS), a greater number of $CD34^+CD38^-$ cells underwent differentiation. Even at 15%, however, some positive effect was maintained, as observed by the presence of $CD34^+CD38^-$ cells in the sample cultured in 15% FCS.

In contrast, in the neutral elutriated HCC-14 cell culture system, the presence of sera diluted the $CD34^+CD38^-$ cells in a concentration-dependent manner. Together, these findings demonstrate how sera were used to fine-tune the difference between a positive readout and a negative readout in the extinction assay. In addition, when this extinction assay was carried out using sera-free media (Bit Medium in FIG. 5), the percentage of $CD34^+CD38^-$ cells did not decrease as rapidly as it did in those samples cultured in sera-containing media.

Example 3

Functional Expression Cloning Strategy for the Identification of Compounds that Modulate Differentiation of Hematopoietic Cells Based on the above findings, a functional expression cloning strategy was designed to identify factors that modulate hematopoietic stem cell and progenitor cell differentiation. In general, a cDNA expression library was generated from positive HBVECs. The cDNA library members from the positive cell line were placed into the neutral cell line of elutriated fraction HCC-14, and the library was screened using the above-described $CD34^+CD38^-$ cell extinction assay. Based on the estimation that there are as many as approximately 100,000 human genes, and if a 1% sensitivity is desired in the extinction assay, the genes can be put into cells that form colonies such that there are 40 colonies per well of a 96-well tissue culture plate. A gene that modulates hematopoietic stem cell or hematopoietic progenitor cell differentiation that is expressed at a ratio of 1 in 40 in the extinction assay would confer, based on the number of cells in the assay, approximately a 2.5% reading for a positive well containing a gene that modulates cell differentiation. As shown in FIGS. 3 and 4, a 2.5% reading for a positive well is within the range of sensitivity of the extinction assay.

Figure 6:
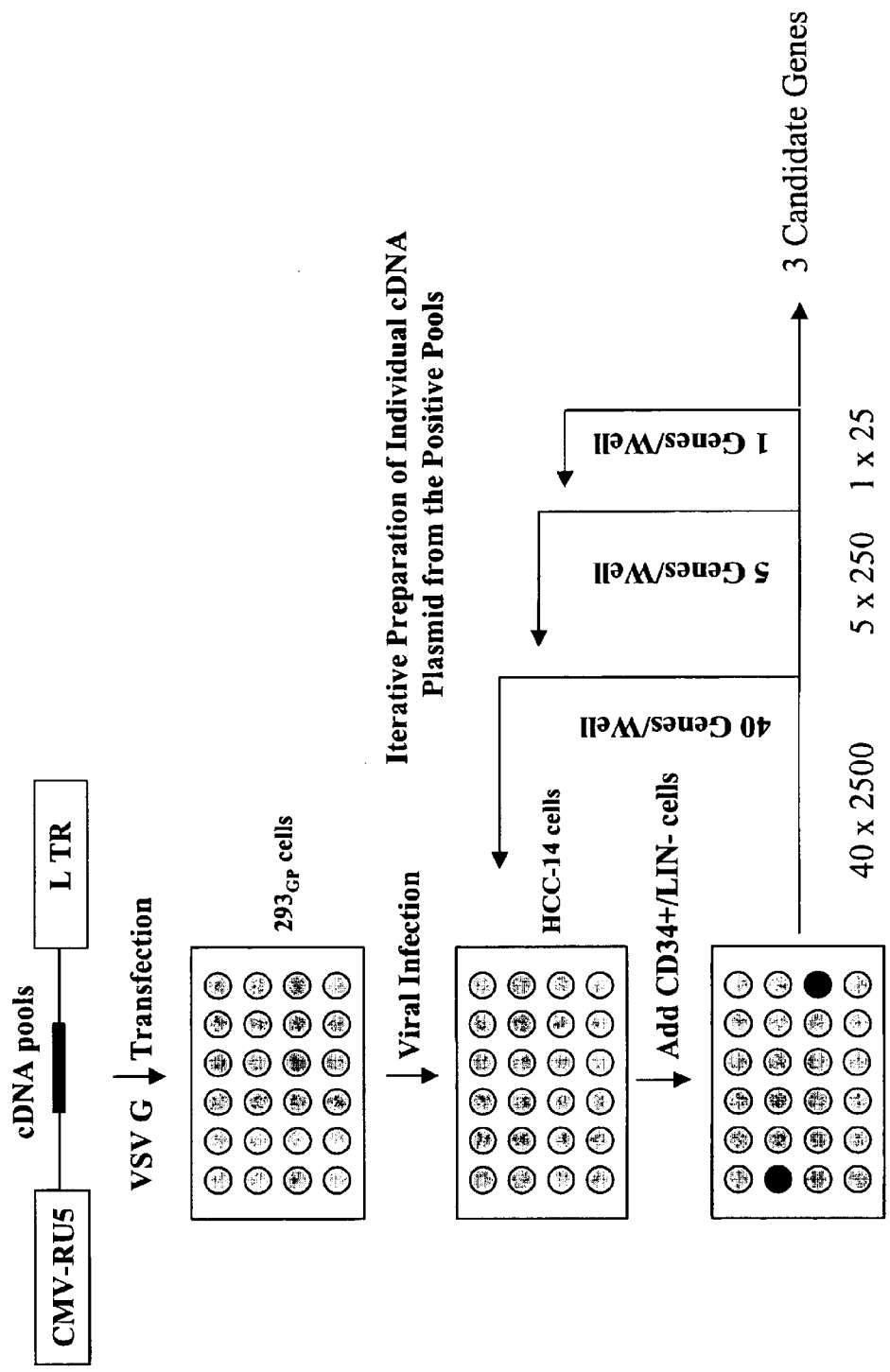
FIG. 6 is a schematic representation of the functional screening strategy for the identification of genes that encode polypeptides that modulate differentiation of hematopoietic cells.

The strategy for the cDNA functional screening assay is depicted schematically in FIG. 6. A pool of retroviral vectors containing the cDNA molecules generated from the positive HBVECs, and flanked by CMV RU 5 LTRs was created. These retroviral vectors were co-transfected with a vector encoding the VSV G gene into 293 cells (a packaging cell line). Retroviruses were harvested from the 293 cells and the HCC-14 cells were infected with the retroviruses. This infection protocol inserted the cDNA molecules from the positive cell line into the HCC-14 neutral cells at approximately 40 cDNA molecules per well. Two days after retroviral infection, $CD34^{+/-}CD38^-Lin^-$ cells, selected by immuno-magnetic selection with a $lin^-$ cocktail (containing antibodies to CD2, CD3, CD 14, CD16, CD19, CD56, CD66B, and GlyA) were added on top of the infected cells.

After 6 weeks of culture in the extinction assay, cells were analyzed by flow cytometry to see whether $CD34^+CD38^-$ cells were present in each well, and to look for positive wells where the population of $CD34^+CD38^-$ cells was maintained or increased in number, as would be observed using an HBVEC positive fraction in the extinction assay (see FIG. 3). Wells that contained a population of $CD34^+CD38^-$ cells that was maintained or increased were more thoroughly analyzed by decreasing the number of genes in the well and repeating the extinction assay. For example, when a well was identified as containing potential modulators of hematopoietic stem cell differentiation, the retroviruses identified as potential modulators were re-infected into HCC-14 cells at a more dilute concentration, such that each well of the tissue culture plate contained five genes encoding potential differentiation modulators. The extinction assay was then repeated to determine if the relative concentration of cells containing an effector gene would decrease the extinction of the $CD34^+CD38^-$ cells. The process was repeated again, such that each well contained one gene.

Figure 7:
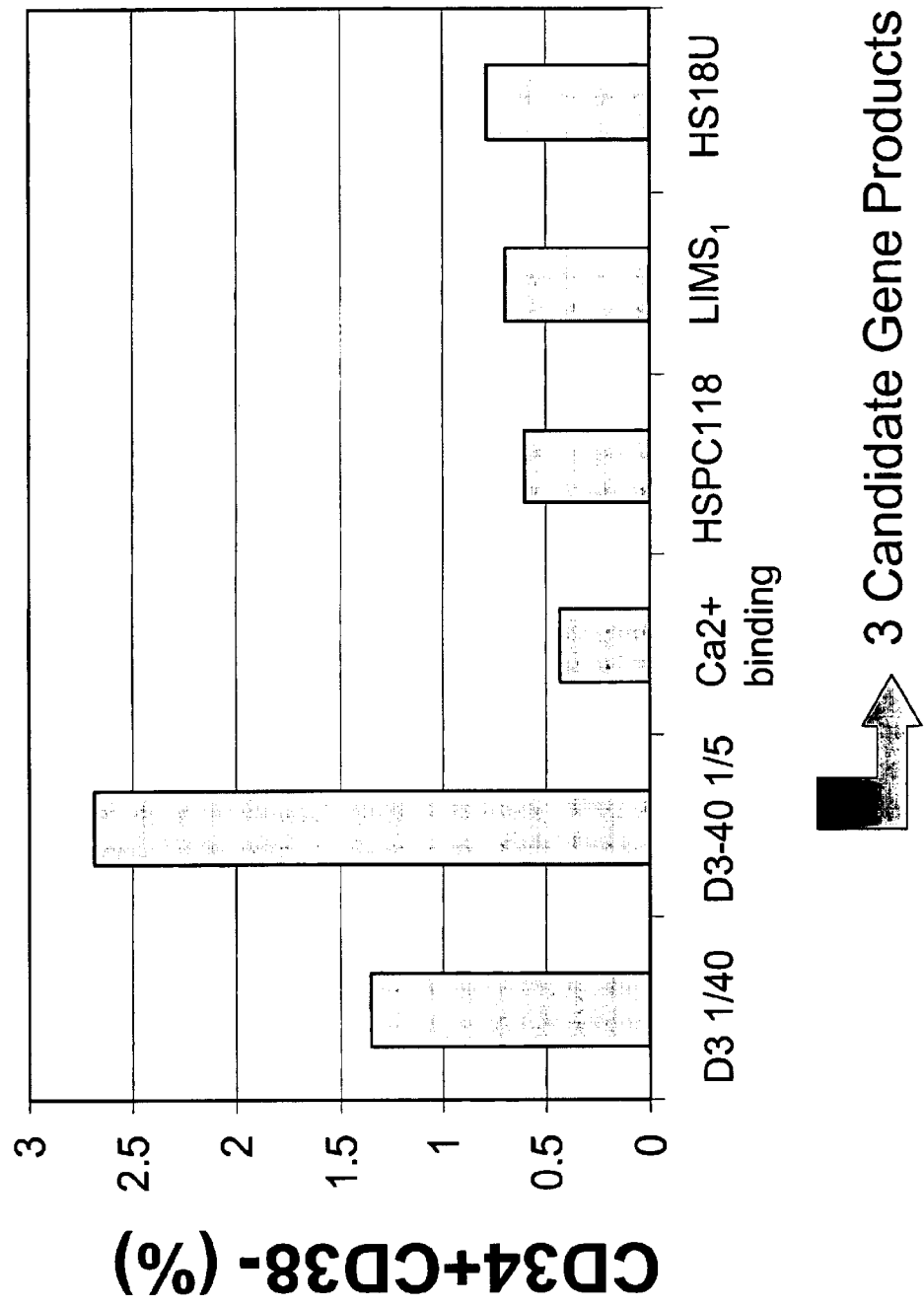
FIG. 7 is a graph of the percent of $CD34^+CD38^-$ cells present after 6 days in a co-culture of cells containing candidate differentiation modulating polypeptides (D3 1/40 and D3-40 1/5) or control polypeptides ($Ca^{2+}$ binding protein, HSPC118, $LIMS_1$, or HS18U).

As an example of the screening assay, the molecules contained in well D3-40, as shown in FIG. 7, were candidates that gave a positive signal when present in the 1 cDNA in 40 cDNAs stage of the screen. These candidates were then retested at a 1 cDNA in 5 cDNAs ratio range (such that the complexity of the cDNA molecules was 8 times lower than the complexity of the cDNA molecules in the 1:40 sample; D3-40 ⅕ in FIG. 7). As shown in FIG. 7, the signal indicating the presence of a molecule(s) that modulates differentiation increased in the screen when used in the 1 in 5 range. Also shown in FIG. 7 are four other cDNA molecules encoding gene products that were used as controls. Compared to the controls, the cDNAs in wells D3 1/40 and D3-40 ⅕ had a positive effect, respectively, on the prevention of differentiation of $CD34^+CD38^-$ cells.

In total, three genes were sequenced out of the 5 genes that were in the D3-40 1 in 5 pool. One of the genes was extracellular matrix protein, a known gene. Another gene was a novel small protein. The third gene was IGFBP-3 with a partial missing carboxyl terminus. This gene encoded an IGFBP polypeptide fragment containing amino acids 1–182, and missing the 110 amino acids at the carboxyl terminus. This IGFBP-3 gene was then confirmed to decrease differentiation of $CD34^+CD38^-$ cells, using the extinction assay.

Example 4

Expression of IGFs and IGFBPs in Undifferentiated Hematopoietic Cells

As a result of the identification of IGFBP-3 as an anti-differentiation factor, the expression pattern for IGFs and IGFBPs in $CD34^{+/-}CD38^-Lin^-$ cells was examined. Expression of IGF-1, IGF-2, and IGFBP-1 through -6 in $CD34^{+/-}CD38^-Lin^-$ cells was examined by RT-PCR at 0.5, 7, 7.5, 14, and 14.5 days of culture. At time points 7 and 14 days, the cell population ($CD34^{+/-}CD38^-$) was assessed for expression of each of the IGFs and IGFBPs. At time points 0.5, 7.5, and 14.5, the population was selected for those cells that were $CD34^{+/-}CD38^-Lin^-$, and only those cell that were $CD34^{+/-}CD38^-Lin^-$ were allowed to remain in culture. After selection, the cell population was again assessed for expression of each of the IGFs and IGFBPs. This selection and isolation process was performed in order to determine which IGFs or IGFBPs were produced in the $CD34^{+/-}CD38^-Lin^-$ cell population.

Figure 8:
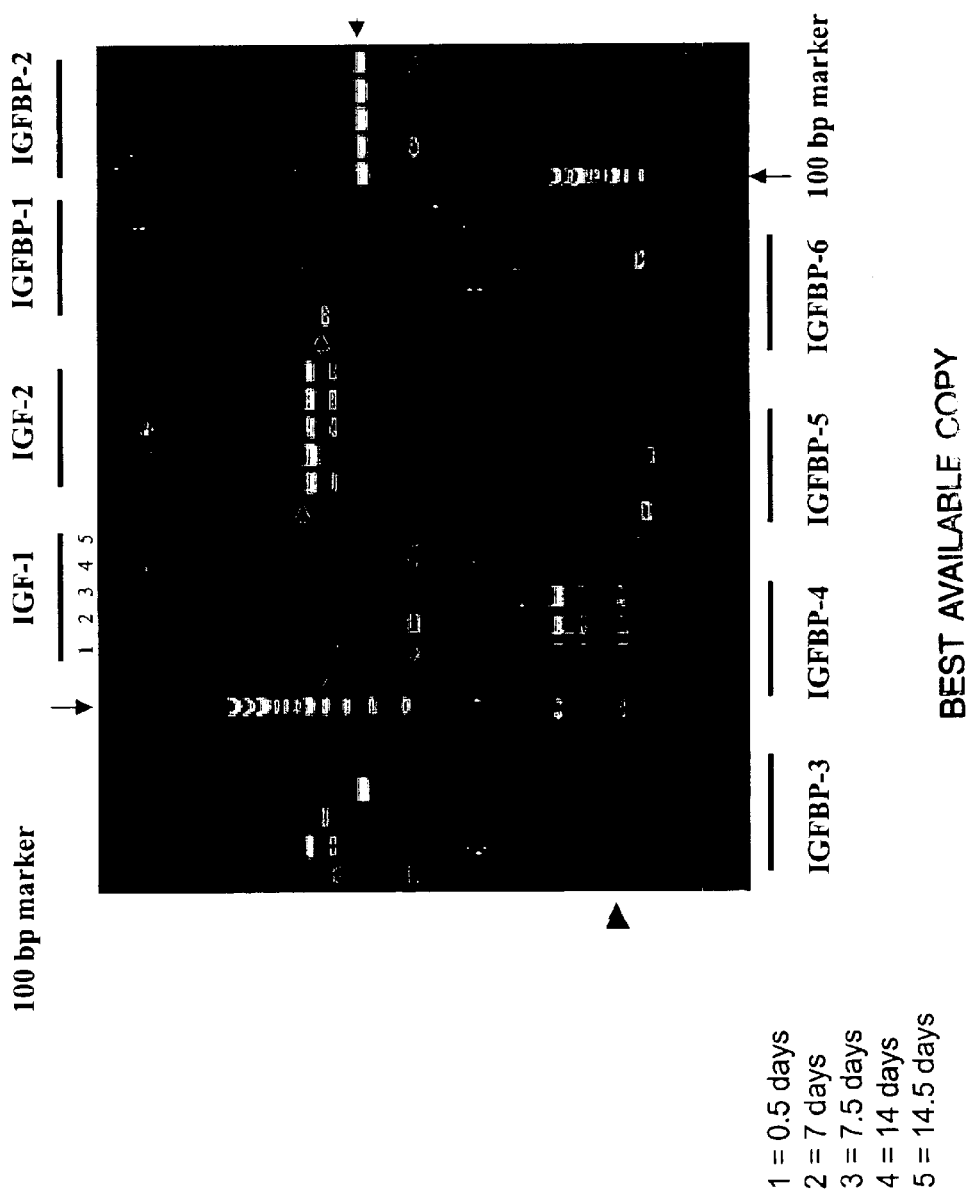
FIG. 8 is a photographic image of an electrophoretic gel showing IFG-1, IGF-2, IGFBP-1, IGFBP-2, IGFBP-3, IGFBP-4, IGFBP-5, and IGFBP-6 expression levels in $CD34^+CD38^-$ cells, as determined by RT-PCR. Expression levels were determined at five time points for each sample, represented by 1–5 (1=0.5 days, 2=7 days, 3=7.5 days, 4=14 days, and 5=14.5 days).

As shown in FIG. 8, there was a slight positive signal for the expression of IGF-1 at day 0.5, after which, expression was low but did exist through day 14.5. IGF-2 was expressed at day 0.5, and it remained expressed through day 14.5. Since the $CD34^{+/-}CD38^-Lin^-$ cells were selected and re-separated, the differentiation factor in these cells was expressed in the more primitive lin⁻ compartment of the cell population, although expression may not be limited to the more primitive compartment.

Turning to the expression pattern of IGFBPs in $CD34^{+/-}CD38^-Lin^-$ cells, IGFBP-1 was expressed at day 0.5 but was not expressed at later time points. IGFBP-2 was expressed very strongly in both $CD34^{+/-}CD38^-$ and $CD34^{+/-}CD38^-Lin^-$ cell populations, both initially and through day 14.5. IGFBP-3, which is the polypeptide identified in the above-described screen, was essentially absent in the $CD34^{+/-}CD38^-Lin^-$ cells. In addition, IGFBP-4 was slightly expressed in $CD34^{+/-}CD38^-$ and $CD34^{+/-}CD38^-Lin^-$ cell populations. Expression of IGFBP-5 varied from days 0.5 to 14.5, and IGFBP-6 expression increased at day 14, and decreased after selection and separation at day 14.5, signifying that at this point in culture IGFBP-6 did not reside in the lin⁻ population of cells.

Example 5

Comparison of IGF and IGFBP Expression Patterns in HBVEC Cells and HCC-14 Cells

Figure 9:
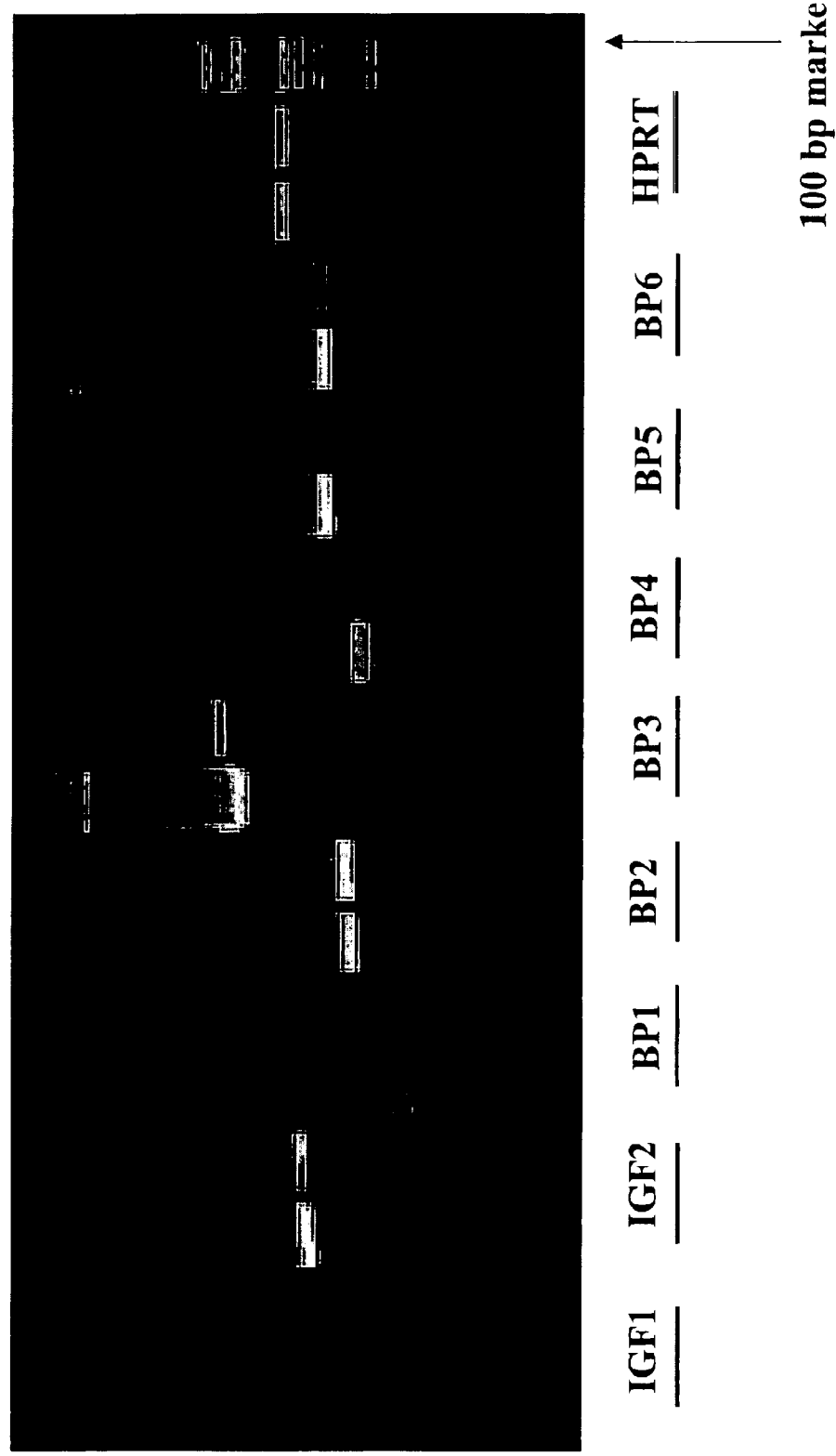
FIG. 9 is a photographic image of an electrophoretic gel showing IFG-1, IGF-2, IGFBP-1, IGFBP-2, IGFBP-3, IGFBP-4, IGFBP-5, and IGFBP-6 expression levels in HBVECs (+) and the elutriated HCC-14 cell fraction (=), as determined by RT-PCR. Hypoxanthine phosphoribosyl transferase (HPRT) is an internal control for the RT-PCR reaction.

The expression of IGFs and IGFBPs in HBVECs and elutriated cell fraction HCC-14 was next examined. As shown in FIG. 9, HBVECs ((+) cells) and HCC-14 cells ((=) cells) were assessed by RT-PCR for expression of each of IGF-1 and -2, and for IGFBP-1 through -6. IGF-1 was slightly expressed in the positive HBVECs, and was not expressed in the neutral HCC-14 cell line. IGF-2 was expressed in both the positive and neutral cell types. IGFBP-1 was expressed in the positive cells, but was not expressed in the neutral cell line. IGFBP-2 was expressed in both cell types. IGFBP-3 was expressed very strongly in the positive cells, and was expressed at lower levels in the neutral cell line. IGFBP-4 was expressed in the positive cells, and was expressed at very low levels in the neutral cells. IGFBP-5 was expressed in the positive cells and was not expressed in the neutral cells. And IGFBP-6 was expressed in positive cells, and was expressed at very low levels in the neutral cells. These results demonstrate that there is differential expression of IGFs and IGFBPs in the positive and neutral cell populations.

Example 6

Figure 10:
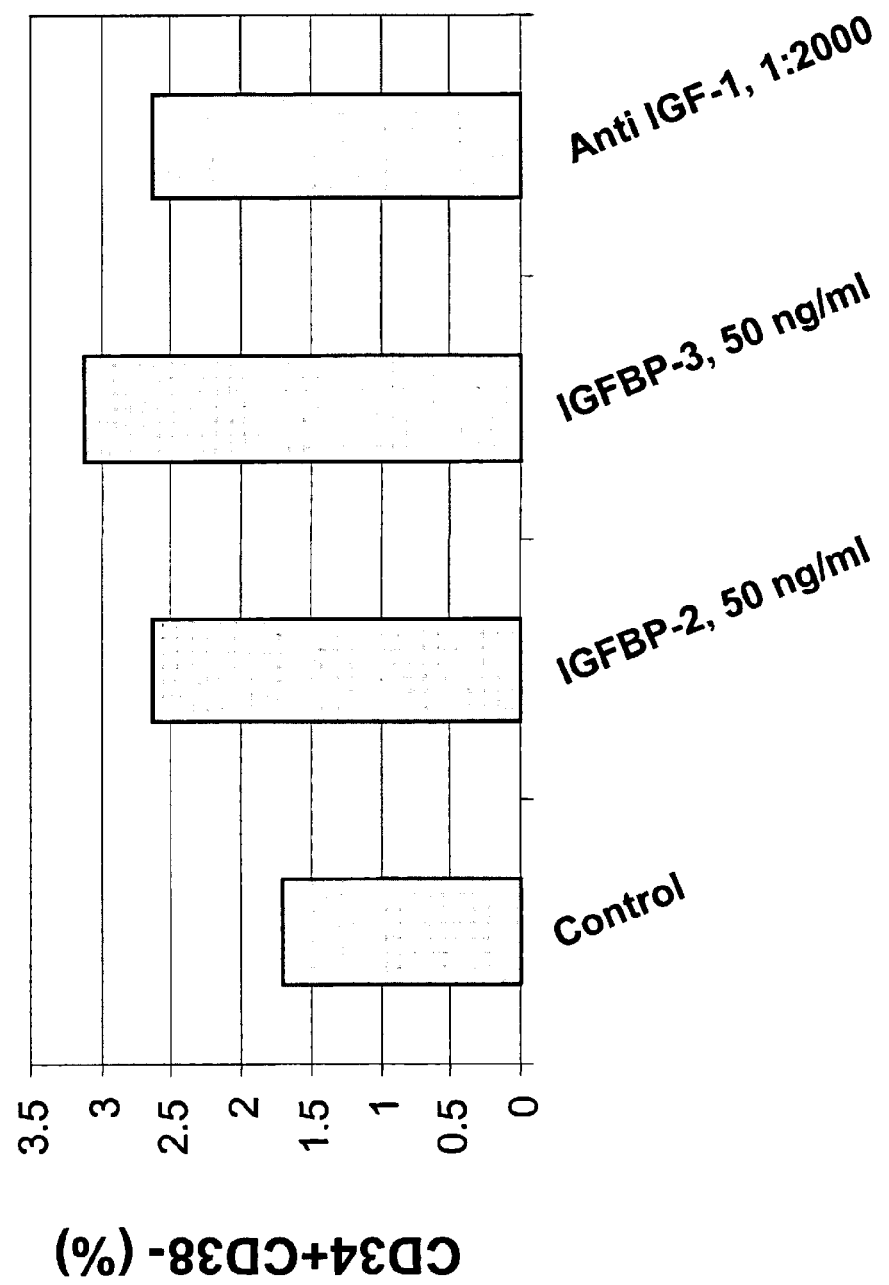
FIG. 10 is a graph of the effect of exogenously added IGFBP-2, IGFBP-3, or an antibody to IGF-1 on the percent of $CD34^+CD38^-$ cells present in a suspension that does not contain HBVECs.

Modulation of Hematopoietic Cell Differentiation Using IGFBPs and Antibodies to IGFs Next, the effect of exogenously added IGFBP-2, IGFBP-3, or antibody to IGF-1 on the population of $CD34^+CD38^-$ cells was determined. This assay was performed by adding IGFBP-2, IGFBP-3, or antibody to IGF-1 to a culture of $CD34^{+/-}CD38^-Lin^-$ cells, and assaying for $CD34^+CD38^-$ cells after 6 days. As shown in FIG. 10, relative to a control culture of $CD34^{+/-}CD38^-Lin^-$ cells, addition of IGFBP-2, IGFBP-3, and antibody to IGF-1, at the indicated concentrations, each increased the number of $CD34^+CD38^-$ cells in the culture.

Example 7

Modulation of Endogenous IGF Activity Using Polypeptides that Bind IGF

The endogenous activity of IGF can be altered in a number of ways in order to modulate the differentiation of cultured hematopoietic stem cells and hematopoietic progenitor cells. For example, polypeptides that bind to IGF, for example, an IGFBP can be administered to cultured hematopoietic stem cells or progenitor cells. As shown in FIG. 10, such polypeptides can be added directly to the cultures, and their effect on the percentage of $CD34^+CD38^-$ cells that remain in the culture over time, assayed, for example, by flow cytometry, is determined. Addition of IGFBPs to the hematopoietic stem cell culture results in an increase in the number of $CD34^+CD38^-$ cells, thereby resulting in a decrease in the differentiation of the hematopoietic stem cell cultures, compared to cultures that were not administered the polypeptide.

Optionally, acid-labile subunit is administered to the hematopoietic stem cell and progenitor cell cultures, along with the IGFBP. ALS is produced according to standard molecular biology methods, as described, for example by Ausubel et al. (supra). This polypeptide forms a ternary complex with IGFs and IGFBPs, for example IGFBP3 or IGFBP5. Formation of such a ternary complex can be used to modulate differentiation of hematopoietic stem cells and hematopoietic progenitor cells, by decreasing the amount of free IGF.

Cell lines that produce a polypeptide, for example, IGFBP or acid-labile subunit, for use in modulation of differentiation of hematopoietic stem or progenitor cells may be generated, and the polypeptide can be purified from the cells and used to modulate differentiation.

For protein expression, eukaryotic and prokaryotic expression systems may be generated in which IGFBP or acid-labile subunit gene sequences are introduced into a plasmid or other vector, and transformed into living cells. Constructs in which IGFBP or acid-labile subunit cDNAs containing the entire open reading frames inserted in the correct orientation into an expression plasmid may be used for protein expression. The desired IGF or IGFBP cDNA sequences can be obtained through the following GenBank accession numbers: IGF1 (NM_000618); IGF2 (NM_000612); IGFBP1 (M27544); IGFBP2 (M35410); IGFBP3 (NM_000598); IGFBP4 (NM_008650); IGFBP5 (XM_002635); IGFBP6 (M62402); ALS (XM_012578). Alternatively, portions of IGFBP or acid-labile subunit gene sequences, including wild-type or mutant IGFBP or acid-labile subunit sequences, may be inserted. Since IGFBP and acid-labile subunit protein expression modulates differentiation, it may be desirable to express the protein under the control of an inducible promoter.

Typical expression vectors contain promoters that direct the synthesis of large amounts of mRNA corresponding to the inserted IGFBP or acid-labile subunit nucleic acid in the plasmid-bearing cells. They may also include eukaryotic or prokaryotic origin of replication sequences allowing for their autonomous replication within the host organism, sequences that encode genetic traits that allow vector-containing cells to be selected for in the presence of otherwise toxic drugs, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Expression of foreign sequences in bacteria such as *Escherichia coli* requires the insertion of the IGFBP or acid-labile subunit nucleic acid sequence into a bacterial expression vector. Such plasmid vectors contain several elements required for the propagation of the plasmid in bacteria, and for expression of the DNA inserted into the plasmid. Propagation of only plasmid-bearing bacteria is achieved by introducing, into the plasmid, selectable marker-encoding sequences that allow plasmid-bearing bacteria to grow in the presence of otherwise toxic drugs. The plasmid also contains a transcriptional promoter capable of producing large amounts of mRNA from the cloned gene. Such promoters may be (but are not necessarily) inducible promoters that initiate transcription upon induction. The plasmid also desirably contains a polylinker to simplify insertion of the gene in the correct orientation within the vector.

Once the appropriate expression vectors containing an IGFBP or acid-labile subunit gene, or fragment, fusion, or mutant thereof, are constructed, they are introduced into an appropriate host cell by transformation techniques, including calcium phosphate transfection, DEAE-dextran transfection, electroporation, microinjection, protoplast fusion, liposome-mediated transfection, and cell penetrating peptides. The host cells that are transfected with the vectors of this invention may include (but are not limited to) *E. coli* or other bacteria, yeast, fungi, insect cells (using, for example, baculoviral vectors for expression), or cells derived from mice, humans, or other animals. Mammalian cells can also be used to express the IGFBP or acid-labile subunit polypeptide using a vaccinia virus expression system described, for example, in Ausubel et al., supra.

In vitro expression of IGFBP or acid-labile subunit proteins, fusions, polypeptide fragments, or mutants encoded by cloned DNA is also possible using the T7 late-promoter expression system. This system depends on the regulated expression of T7 RNA polymerase, an enzyme encoded in the DNA of bacteriophage T7. The T7 RNA polymerase initiates transcription at a specific 23-bp promoter sequence called the T7 late promoter. Copies of the T7 late promoter are located at several sites on the T7 genome, but none is present in *E. coli* chromosomal DNA. As a result, in T7-infected cells, T7 RNA polymerase catalyzes transcription of viral genes but not of *E. coli* genes. In this expression system, recombinant *E. coli* cells are first engineered to carry the gene encoding T7 RNA polymerase next to the lac promoter. In the presence of IPTG, these cells transcribe the T7 polymerase gene at a high rate and synthesize abundant amounts of T7 RNA polymerase. These cells are then transformed with plasmid vectors that carry a copy of the T7 late promoter protein. When IPTG is added to the culture medium containing these transformed *E. coli* cells, large amounts of T7 RNA polymerase are produced. The polymerase then binds to the T7 late promoter on the plasmid expression vectors, catalyzing transcription of the inserted cDNA at a high rate.

Since each *E. coli* cell contains many copies of the expression vector, large amounts of mRNA corresponding to the cloned cDNA can be produced in this system and the resulting protein can be radioactively labeled. Plasmid vectors containing late promoters and the corresponding RNA polymerases from related bacteriophages such as T3, T5, and SP6 may also be used for in vitro production of proteins from cloned DNA. *E. coli* can also be used for expression using an M13 phage such as mGPI-2. Furthermore, vectors that contain phage lambda regulatory sequences, or vectors that direct the expression of fusion proteins, for example, a maltose-binding protein fusion protein or a glutathione-S-transferase fusion protein, also may be used for expression in *E. coli*.

Eukaryotic expression systems are useful for obtaining appropriate post-translational modification of expressed proteins. Transient transfection of a eukaryotic expression plasmid allows the transient production of IGFBP or acid-labile subunit polypeptides by a transfected host cell. IGFBP or acid-labile subunit polypeptides may also be produced by a stably-transfected mammalian cell line. A number of vectors suitable for stable transfection of mammalian cells are available to the public (e.g., see Pouwels et al., *Cloning Vectors: A Laboratory Manual,* 1985, Supp. 1987), as are methods for constructing such cell lines (see e.g., Ausubel et al., supra). In one example, a cDNA encoding an IGFBP or acid-labile subunit protein, fusion, mutant, or polypeptide fragment is cloned into an expression vector that includes the dihydrofolate reductase (DHFR) gene. Integration of the plasmid and, therefore, integration of the IGFBP or acid-labile subunit encoding gene into the host cell chromosome is selected for by inclusion of 0.01–300 $\mu$M methotrexate in the cell culture medium (as described, Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al., supra. These methods generally involve extended culture in medium containing gradually increasing levels of methotrexate. The most commonly used DHFR-containing expression vectors are pCVSEII-DHFR and pAdD26SV(A) (described, for example, in Ausubel et al., supra). The host cells described above or, desirably, a DHFR-deficient CHO cell line (e.g., CHO DHFR⁻ cells, ATCC Accession No. CRL 9096) are among those most preferred for DHFR selection of a stably-transfected cell line or DHFR-mediated gene amplification.

Another preferred eukaryotic expression system is the baculovirus system using, for example, the vector pBacPAK9, which is available from Clontech (Palo Alto, Calif.). If desired, this system may be used in conjunction with other protein expression techniques, for example, the myc tag approach described by Evan et al. (*Mol. Cell Biol.* 5:3610–3616, 1985).

Once the recombinant protein is expressed, it can be isolated from the expressing cells by cell lysis followed by protein purification techniques, such as affinity chromatography. Depending on the polypeptide to be isolated, an antibody directed against an IGFBP or acid-labile subunit polypeptide can be attached to a column and used to isolate the recombinant IGFBP or acid-labile subunit proteins. Lysis and fractionation of IGFBP- or acid-labile subunit protein-harboring cells prior to affinity chromatography may be performed by standard methods (see e.g., Ausubel et al., supra). Once isolated, the recombinant protein can, if desired, be purified further by e.g., by high performance liquid chromatography (HPLC; e.g., see Fisher, *Laboratory Techniques in Biochemistry and Molecular Biology,* Work and Burdon, Eds., Elsevier, 1980).

Polypeptides of the invention, particularly short IGFBP or acid-labile subunit fragments and longer fragments of the N-terminus and C-terminus of the IGFBP or acid-labile subunit polypeptide, can also be produced by chemical synthesis (e.g., by the methods described in *Solid Phase Peptide Synthesis,* 2nd ed., 1984, The Pierce Chemical Co., Rockford, Ill.). These general techniques of polypeptide expression and purification can also be used to produce and isolate useful IGFBP or acid-labile subunit polypeptide fragments or analogs, as described herein.

Those skilled in the art of molecular biology will understand that a wide variety of expression systems may be used to produce the recombinant IGFBP or acid-labile subunit polypeptides. The precise host cell used is not critical to the invention. The IGFBP or acid-labile subunit proteins may be produced in a prokaryotic host (e.g., *E. coli*) or in a eukaryotic host (e.g., *S. cerevisiae,* insect cells such as Sf9 cells, or mammalian cells such as COS-1, NIH 3T3, or HeLa cells). These cells are commercially available from, for example, the American Type Culture Collection, Rockville, Md. (see also Ausubel et al., supra). The method of transformation and the choice of expression vehicle (e.g., expression vector) will depend on the host system selected. Transformation and transfection methods are described, e.g., in Ausubel et al., supra, and expression vehicles may be chosen from those provided, e.g. in Pouwels et al., *Cloning Vectors: A Laboratory Manual,* 1985, Supp. 1987.

IGFBP or Acid-Labile Subunit Polypeptide Fragments

Polypeptide fragments that incorporate various portions of IGFBP or acid-labile subunit proteins are useful in the modulation of differentiation of primary stem cells, for example, hematopoietic stem cells, or hematopoietic progenitor cells, as demonstrated by the determination in the above-described screen that an IGFBP-3 fragment is an anti-differentiation factor. Methods for generating such fragments are well known in the art (see, for example, Ausubel et al., supra) using the nucleotide sequences provided herein. For example, an IGFBP or acid-labile subunit protein fragment may be generated by PCR amplifying the desired fragment using oligonucleotide primers designed based upon the IGFBP or acid-labile subunit nucleic acid sequences. Desirably the oligonucleotide primers include unique restriction enzyme sites that facilitate insertion of the fragment into the cloning site of a mammalian expression vector. This vector may then be introduced into a mammalian cell by artifice by the various techniques known in the art and described herein, resulting in the production of an IGFBP or acid-labile subunit gene fragment.

Example 8

Modulation of Endogenous IGF Activity Using Antibodies

In order to increase the number of differentiated stem cells in a hematopoietic stem cell culture, the culture can be administered an antibody that binds to an IGFBP. As demonstrated above, an IGFBP, for example, IGFBP-3 is an anti-differentiation factor. Therefore, inhibiting the activity of IGFBP, for example, by adding an antibody against an IGFBP to the culture, decreases the number of undifferentiated CD34⁺CD38⁻ cells in the culture.

Example 9

Assays for Compounds that Modulate IGF Activity

Compounds that modulate endogenous IGF activity may be identified using any of the methods described herein (or any analogous method known in the art). For example, a candidate compound is administered to a hematopoietic stem cell or progenitor cell culture. The number of CD34⁺CD38⁻ cells in the culture is monitored over time. A compound that increases the number of CD34⁺CD38⁻ cells is a compound that decreases the differentiation of hematopoietic stem cells, and a compound that decreases the number of CD34⁺CD38⁻ cells in the culture is a compound that increases the differentiation of hematopoietic stem and progenitor cells.

The identification of compounds that bind IGF can also be identified using a fluorescence polarization assay. In this assay, an interaction between two polypeptides is measured. One polypeptide is labeled with a fluorescent tag, and this polypeptide emits nonpolarized light when excited with polarized light. Upon an interaction of the tagged polypeptide with another polypeptide, the polarization of emitted light is altered, and can be detected. Polypeptides identified through this assay to bind IGF can be used to modulate differentiation of hematopoietic cells.

This fluorescence polarization assay can also be used to identify a compound that disrupts the interaction between two polypeptides, for example, an IGF and an IGFBP. As stated above, upon binding of a tagged peptide to another polypeptide, the polarization of light emitted by the tagged peptide is altered. Therefore, in a sample in which a compound does not inhibit the interaction between the two polypeptides, the polarization of light emitted by the tagged polypeptide will be altered. Conversely, in a sample in which a compound does inhibit the interaction between the two polypeptides the polarization of light emitted by the peptide will not be altered. Thus, the fluorescence polarization assay can be used to identify compounds that modulate differentiation of hematopoietic stem and progenitor cells.

The interaction between two polypeptides may be assessed by other means known to those skilled in the field of molecular biology. For example, the interacting proteins may be co-immunoprecipitated using an antibody that recognizes either of the polypeptides, using methods commonly known in the art.

Example 10

Test Compounds

In general, drugs for modulating the endogenous activity of IGF, and the differentiation of hematopoietic stem cells may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their IGF modulatory activities should be employed whenever possible.

When a crude extract is found to modulate (i.e., stimulate or inhibit) IGF activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that modulates endogenous IGF activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art.

Example 11

Modulation of Differentiation of Primary Stem Cells in Culture by Reducing Cells that Produce IGF from the Culture The potential for hematopoietic stem cells in culture to undergo differentiation can be decreased by decreasing exposure of the cells to IGF. One method that can be used to decrease exposure of the cells to IGF is to remove those cells that are producing IGF from the culture. This can be done, for example, through the use of a cell sorter, where those cells that express (and then secrete) IGF are removed from those cells that do not express IGF. The cells that were not removed in the cell sorting process are then returned to the culture, and allowed to continue growing. This cell sorting process is repeated until the population of undifferentiated hematopoietic stem cells reaches the desired number.

In addition, cells that produce IGF in a culture population can be selectively targeted and killed, thereby reducing the differentiation of primary stem cells in the culture. This selective targeting and killing of the IGF-producing cells can be carried out, for example, by adding an antibody with complement to kill the IGF-producing cells.

Example 12

Expansion of $CD34^+CD38^-$ Cells and Use in Engraftment Studies

Expansion of $CD34^+CD38^-$ cells in a culture containing a mixture of cells can be achieved by treatment under various conditions. Table 1 presents data from an expansion culture experiment in which cells are cultured under various conditions and the expansion of $CD34^+CD38^-$ cells is monitored. Table 1 presents the total cell number and the $CD34^+CD38^-Lin^-$ cell number before treatment and the total cell number and $CD34^+CD38^-$ cell number after treatment with anti-TGF-$\beta$1, antisense BP-3, sense BP-3, anti-BP-3, and TGF-$\beta$1. Note that the TGF-$\beta$1 culture barely grows while the other conditions produce roughly the same number of cells.

TABLE 1

| SERUM FREE | Total Cell No. | CD34+CD38−Lin+ | CD34+CD38− |
|---|---|---|---|
| Before Culture | $5.9 \times 10^5$ | $5.5 \times 10^4$ | |
| Control | $4.54 \times 10^6$ | | $7.0 \times 10^5$ |
| Anti-TGFb1 | $4.83 \times 10^6$ | | $7.9 \times 10^5$ |
| Antisense BP3 | $4.83 \times 10^6$ | | $7.4 \times 10^5$ |
| Sense BP3 | $4.80 \times 10^6$ | | $7.6 \times 10^5$ |
| Anti-BP3 | $4.58 \times 10^6$ | | $6.7 \times 10^5$ |
| TGF-b1 | $1.77 \times 10^6$ | | $1.3 \times 10^5$ |

Figure 13:
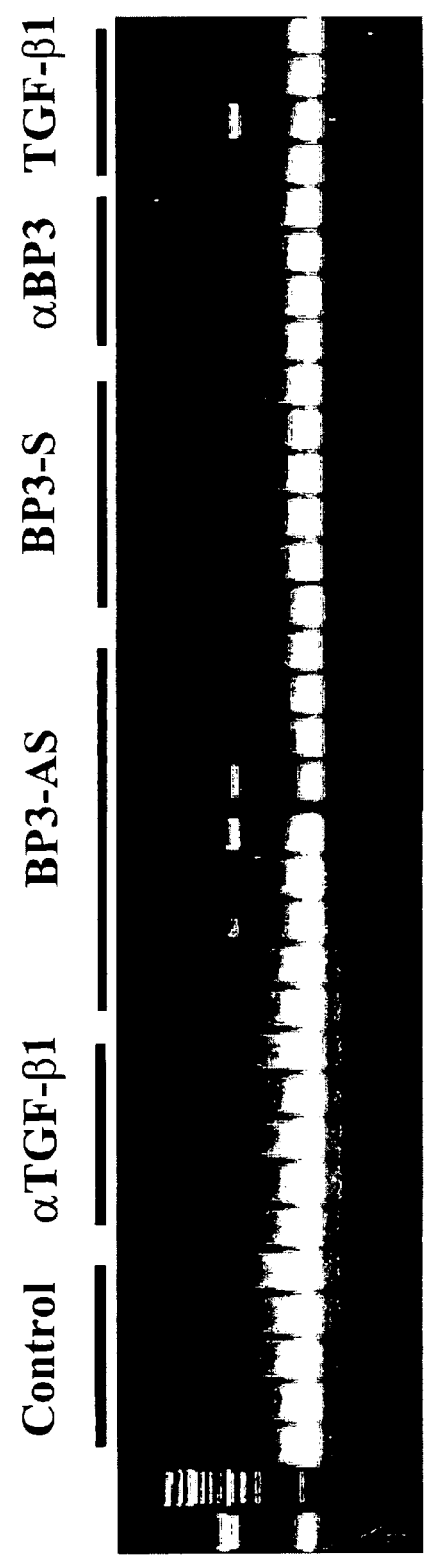
FIG. 13 is a scanned image of an electrophoretic gel demonstrating the presence or absence of engrafted human cells in NOD/Scid mice which have received no treatment (control), or have been treated with αTGF-β1 antibody, BP-3 antisense nucleic acid molecules, BP-3 sense nucleic acid molecules, αBP-3 antibody, or TGF-β1. The presence of a higher molecular weight band in lanes 13, 15, 16, and 18 (BP-3 AS treatment), lane 26 (αBP-3 antibody treatment), and lane 31 (TGF-β1 treatment) indicates the presence of engrafted cells.

The results of engraftment studies using human cells grown in expansion cultures (represented in Table 1) which have been engrafted into NOD/Scid mice is presented in Table 2. The same treatments described above were used to treat the human cells prior to engraftment. The percent mortality and percent of surviving mice in which the cells engraft is presented in Table 2. It is noted that the percent mortality of mice engrafted with human cells treated with antisense BP-3 is significantly lower than the percent mortality of mice engrafted with human cells that had been exposed to the other treatments. Furthermore, the percent of surviving mice that engrafted with human cells treated with antisense BP-3 was also significantly higher. FIG. 13 is a scanned electrophoretic gel which indicates the presence of the engrafted cells in the mice.

TABLE 2

| | Mice Injected | % of Mortality | % of Surviving Mice that Engraft |
|---|---|---|---|
| Control | 10 | 60 | 0 (0/4) |
| Anti-TGFb1 | 10 | 50 | 0 (0/5) |
| Antisense BP3 | 10 | 20 | 50 (4/8) |
| Sense BP3 | 10 | 50 | 0 (0/5) |
| Anti-BP3 | 10 | 60 | 25 (1/4) |
| TGF-b1 | 10 | 60 | 25 (1/4) |

Example 13

Antisense Nucleic Acids for the Modulation of Differentiation of Hematopoietic Stem Cells and Hematopoietic Progenitor Cells Antisense-based strategies may be employed to modulate the differentiation of hematopoietic stem cells and hematopoietic progenitor cells. The principle is based on the hypothesis that sequence-specific suppression of gene expression (via transcription or translation) may be achieved by intracellular hybridization between genomic DNA or mRNA and a complementary antisense species. The formation of a hybrid RNA duplex interferes with transcription of the target encoding genomic DNA, or processing, transport, translation, and/or stability of the target mRNA.

Antisense strategies may be delivered by a variety of approaches. For example, antisense oligonucleotides or antisense RNA may be directly administered (e.g., by adding the antisense oligonucleotides or RNA to the culture) to hematopoietic stem cells or hematopoietic progenitor cells in a form that allows uptake into cells. Phenotypic effects, for example, differentiation of the hematopoietic stem cell culture induced by antisense effects are based on changes in criteria such as protein levels, protein activity measurement, and target mRNA levels of IGF, IGFBP, IGF receptor, or acid-labile subunit.

The following antisense oligonucleotides have been designed for use in the modulation of the endogenous activity of IGF activity:

Antisense to IGF-1: 5'-AGA TGC GAG GAG GAC-3' SEQ ID NO: 1

Antisense to IGF-2: 5'-TTC CCC ATT GGG ATT CCC AT-3' SEQ ID NO: 2

Antisense to IGF-1 Receptor: 5'-TCC-TCC-GGA-GCC-AGA-CTT-3' and 5'-TCC GAG GCC AGA CTT-3' SEQ ID NO:3

Antisense to IGFBP-3: 5'-CAT GAC GCC TGC AAC CGG GG-3' SEQ ID NO: 4

Antisense to IGFBP-3: 5'-CAA CAC CAT CTT CTC-3' SEQ ID NO: 5

The antisense oligonucleotides are synthesized by methods known to those of skill in the art, and can be generated to contain modified phosphodiester linkages, such as phosphorothioate or methylimino substituted oligonucleotides. The antisense oligonucleotides are administered to a hematopoietic stem cell culture by directly adding them to the culture media (e.g., to a final concentration of 0.6 PM). Alternatively, uptake of antisense oligonucleotides can be aided using cationic lipid cytofection GSV as a transfection reagent. A phosphothiolated IGFBP3 specific sense oligo (5'-CCC CGG TTG CAG GCG TCA TG-'3; SEQ ID NO: 6) was also designed for use in the modulation of the endogenous activity of IGF activity. The oligos can be dissolved in sterile phosphate buffered saline and stored at 4° C. as a working stock.

TGF-β1 treatment experiments were performed in the presence or absence of IGFBP3 sense or antisense oligonucleotides. The oligomers were added directly to cell cultures at a concentration of 20 μg/mL.

HPP-CFC assays were performed by adding the sense or antisense oligomers to methylcellulose medium at a final concentration of 50 μg/mL. The Lin− cells were then plated at 150 of CD34+CD38−Lin−/mL/6 cm plate.

Retroviral vectors, adenoviral vectors, adeno-associated viral vectors, or other viral vectors with the appropriate tropism for cells likely requiring modulation of differentiation (for example, primary stem cells, including hematopoietic stem cells, and hematopoietic progenitor cells) may be used as a gene transfer delivery system for an antisense IGF, IGFBP, or acid-labile subunit gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277–1278, 1991; Cornetta et al., Nucleic Acid Research and Molecular Biology 36:311–322, 1987; Anderson, Science 226:401–409, 1984; Moen, Blood Cells 17:407–416, 1991; Miller et al., BioTechniques 7:980–990, 1989; Le Gal La Salle et al., Science 259:988–990, 1993; and Johnson, Chest 107:77S–83S, 1995).

Retroviral vectors are particularly well developed and have been used in clinical settings (Rosenberg et al., N. Engl. J. Med 323:370, 1990; and Anderson et al., U.S. Pat. No. 5,399,346). Non-viral approaches may also be employed for the introduction of therapeutic DNA into cells otherwise predicted to undergo a modulation in differentiation. For example, antisense IGF, IGFBP, or acid-labile subunit gene constructs may be introduced into a cell by lipofection (Felgner et al., Proc. Natl. Acad. Sci. USA 84:7413, 1987; Ono et al., Neurosci. Lett. 117:259, 1990; Brigham et al., Am. J. Med. Sci. 298:278, 1989; and Staubinger et al., Meth. Enz. 101:512, 1983), the penetratin system (Allinquant et al., J. Cell Biol. 128:919–927, 1995; and Prochiantz, Curr. Opin. Neurobiol. 6:629–634, 1996), asialorosonucoid-polylysine conjugation (Wu et al., J. Biol. Chem. 263:14621, 1988; and Wu et al., J. Biol. Chem. 264:16985, 1989); or, less desirably microinjection (Wolff et al., Science 247:1465, 1990).

In the therapeutic antisense nucleic acid constructs described, antisense nucleic acid expression can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in hematopoietic cells may be used to direct expression. Enhancers include, without limitation, those that are characterized as tissue- or cell-specific in their expression. Alternatively, if a clone is used as a therapeutic construct, regulation may be mediated by the cognate regulatory sequences or, if desired, by regulatory sequences derived from a heterologous source, including any of the promoters or regulatory elements described above.

Any number of standard assays may be used to detect RNA and protein levels in the primary stem cell cultures or hematopoietic progenitor cell cultures that have been administered an IGF or IGF receptor antisense nucleic acid. For example, RNA levels can be measured using standard Northern blot analysis or RT-PCR techniques. In addition, protein levels can be measured, for example, by standard Western blot analyses or immunoprecipitation techniques. Alternatively, cells administered an antisense IGF or IGF receptor nucleic acid may be examined for cell differentiation, for example, by determining the number of $CD34^+CD38^-$ cells. Antisense oligonucleotides that decrease the production of IGF in the hematopoietic stem cell culture also decrease the differentiation of hematopoietic stem cells.

Alternatively, in order to increase the differentiation of hematopoietic stem cells in culture, antisense IGFBPs, for example, antisense IGFBP-3 oligonucleotides, can be added to the culture. Antisense nucleic acids that increase the number of $CD34^+CD38^-$ cells in the hematopoietic stem cell cultures can be used to increase differentiation of the culture.

All publications and patent applications mentioned in this specification are herein incorporated by reference to the same extent as if each independent publication or patent application was specifically and individually indicated to be incorporated by reference.

What is claimed is:

1. A method of inhibiting differentiation of a cultured $CD34^+CD38^-$ cell, said method comprising the step of altering in said cell the endogenous activity of an insulin-like growth factor by contacting said cell with insulin-like growth factor binding protein-3 to inhibit differentiation of said cell.

2. The method of claim 1, wherein said insulin-like growth factor is insulin-like growth factor-1.

3. The method of claim 2, wherein said insulin-like growth factor is insulin-like growth factor-2.

4. The method of claim 1, wherein said $CD34^+CD38^-$ cell is a hematopoietic progenitor cell.

5. The method of claim 1 tiny of claim 1, wherein said $CD34^+CD38^-$ cell is a primary stem cell.

6. The method of claim 5, wherein said primary stem cell is mammalian.

7. The method of claim 6, wherein said primary stem cell is human.

8. The method of claim 4, wherein said hematopoietic progenitor cell is mammalian.

9. The method of claim 8, wherein said hematopoietic progenitor cell is human.

* * * * *

SEQUENCE LISTING

<160> NUMBER OF SEQ ID NOS: 6

<210> SEQ ID NO 1
<211> LENGTH: 15
<212> TYPE: DNA
<213> ORGANISM: Artificial Sequence
<220> FEATURE:
<223> OTHER INFORMATION: Oligonucleotide

<400> SEQUENCE: 1
agatgcgagg aggac                                            15

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
ttccccattg ggattcccat                                       20

<210> SEQ ID NO 3
<211> LENGTH: 18
<212> TYPE: DNA
<213> ORGANISM: Artificial Sequence
<220> FEATURE:
<223> OTHER INFORMATION: Oligonucleotide

<400> SEQUENCE: 3
tcctccggag ccagactt                                         18

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide

```
-continued

<400> SEQUENCE: 4
catgacgcct gcaaccgggg                                              20

<210> SEQ ID NO 5
<211> LENGTH: 15
<212> TYPE: DNA
<213> ORGANISM: Artificial Sequence
<220> FEATURE:
<223> OTHER INFORMATION: Oligonucleotide

<400> SEQUENCE: 5
caacaccatc ttctc                                                   15

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
ccccggttgc aggcgtcatg                                              20
```